United States Patent [19]

Brenner et al.

[11] Patent Number: 5,340,921
[45] Date of Patent: Aug. 23, 1994

[54] Γ, δT CELL RECEPTOR AND METHODS AND DETECTION

[75] Inventors: Michael B. Brenner, Ashland; Jack L. Strominger, Lexington; Johnathan Seidman, Mitlon; Stephen H. Ip, Framingham; Michael S. Krangel, Newtonville, all of Mass.

[73] Assignees: T Cell Sciences, Inc., Cambridge; The Dana-Farber Cancer Institute, Boston; President & Fellows of Harvard College, Cambridge, all of Mass.

[21] Appl. No.: 16,252

[22] Filed: Feb. 19, 1987

Related U.S. Application Data

[63] Continuation-in-part of Ser. No. 882,100, Jul. 3, 1986, abandoned.

[51] Int. Cl.$^5$ .................. A61K 35/14; C07K 3/00
[52] U.S. Cl. .................. 530/350; 435/7.1; 435/7.24; 530/387.1; 530/388.1; 530/388.75; 530/868; 436/506
[58] Field of Search .............. 435/7, 172.2, 240.27, 435/7.1, 7.24; 436/501, 506, 548, 518; 350/350, 387; 935/101; 530/350, 387.1, 387.5, 388.1, 388.22, 388.75, 389.1, 868

[56] References Cited

U.S. PATENT DOCUMENTS 4,713,332  12/1987  Mak .................................. 435/70

OTHER PUBLICATIONS

Nowill et al., 1986, J. Exp. Med. 163: 1601–1606 [DA].
Lomant and Fairbanks, J. Mol. Biol. 104: 243–261 (1976).
Fabbi et al., Eur. J. Immunol. 15: 821–827 (1985).
Maxam and Gilbert, Meth. Enzymol., 65: 499–560 (1980).
Sanger et al., Proc. Natl. Acad. Sci. U.S.A. 74(12): 5463–5467 (1977).
Maniatis et al., Molecular Cloning, A Laboratory Manual, Cold Spring Harbor Laboratory, Cold Spring Harbor, N.Y. (1982).
DeRobertis and DeRobertis, Cell and Mol. Biology, 7th Ed., Saunders College, Pa. (1980).
Quertermous et al., Science, vol. 231, Jan. 1986, pp. 231–255.
Dialynas et al., PNAS USA, vol. 83, Apr. 1986, pp. 2619–2623.
Sevier et al., Clin. Chem.; vol. 27(11), 1981, pp. 1797–1806.
Kyte, J. Mol. Biol., vol. 157, 1982, pp. 105–132.
Hopp, PNAS USA, vol. 78, Jun. 1981, pp. 3824–3828.
Krissansen et al., EMBO J., vol. 5(8), 1986, pp. 1799–1808.
Elsen et al., Proc. Natl. Acad. Sci. USA, vol. 83, May 1986, pp. 2944–2948.
Pardoll et al., Faseb J. 1: 103–109 (1987).
Reilly et al., Nature 321: 878–880 (Jun. 1986).
Rupp et al., Nature 321: 876–878 (Jun. 1986).
Haars et al., J. Exp. Med. 164: 1–24 (Jul. 1986).
Moingeon et al., Nature 323: 638–640 (Oct. 1986).
Jones et al., Nature 323: 635–638 (Oct. 1986).
Lanier and Weiss, Nature 324: 268 (1986).

(List continued on next page.)

Primary Examiner—Robert J. Hill, Jr.
Assistant Examiner—Laurie Scheiner
Attorney, Agent, or Firm—Pennie & Edmonds

[57] ABSTRACT

The present invention provides purified polypeptides which comprise at least a portion of a δT cell receptor polypeptide, a γT cell receptor polypeptide, a γ, δT cell receptor complex or a γ, γT cell receptor complex. Substances capable of forming complexes with these polypeptides are also provided.

Additionally, methods for detecting T cells which have within them or on their surfaces a polypeptide of the present invention are provided. Moreover, methods for diagnosing immune system abnormalities are provided which comprise measuring in a sample from a subject the number of T cells which have within them or on their surfaces a polypeptide of the present invention.

40 Claims, 14 Drawing Sheets

OTHER PUBLICATIONS

LeFranc et al., Proc. Natl. Acad. Sci. U.S.A. 83: 9596–9600 (1986).
European Patent Application Pub. No. 200, 350, published Nov. 5, 1986.
MacLeod et al., Proc. Natl. Acad. Sci. U.S.A. 83: 6989–6993 (1986).
Brenner et al., Nature (London) 322: 145–149 (1986).
Tunnacliffe et al., EMBO J. 5: 1245–1252 (1986).
LeFranc et al., Cell 45: 237–246 (1986).
Mak, U.S. Patent No. 4,713,332, filed Feb. 6, 1984, issued Dec. 15, 1987.
Royer et al., J. Exp. Med. 160: 947–952 (1984).
Reinherz et al., U.S. Patent No. 4,550,086, filed Feb. 16, 1983, issued Oct. 29, 1985.
Goldenberg, U.S. Patent No. 4,444,744, filed Sep. 3, 1982, issued Apr. 24, 1984.
Allison et al., J. Immunol. 129, 2293–2300 (1982).
Kappler et al., Cell 35, 295–302 (1983).
Acuto et al., J. Exp. Med. 158, 1368–1373 (1983).
Haskins et al., J. Exp. Med. 157, 1149–1169 (1983).
Acuto et al., Cell 34, 717–726 (1983).
Samelson and Schwartz, Immunological Reviews 81, 131–144 (1984).
Hedrick et al., Nature 308, 153–158 (1984).
Yanagi et al., Nature 308, 145–149 (1984).
Saito et al., Nature 312, 36–40 (1984).
Sim et al., Nature 312, 771–775 (1984).
Chien et al., Nature 312, 31–35 (1984).
Siu et al., Cell 37, 393–401 (1984).
Patten et al., Nature 312, 40–46 (1984).
Yoshikai et al. Nature 312, 521–524 (1984).
Yanagi et al., Proc. Natl. Acad. Sci. U.S.A. 82, 3430–3434 (1985).
Hedrick et al., Proc. Natl. Acad. Sci. U.S.A. 82, 531–535 (1985).
Becker et al., Nature 317, 430–434 (1985).
Tonegaw, Scientific American, pp. 122–131 Oct. 1985.
Yague et al., Cell 42, 82–87 (1985).
Blanckmeister et al., J. Exp. Med. 162: 851–863 (1985).
Dembic et al., Nature 320, 232–238 (1986).
Saito et al., Nature 309, 757–762 (1984).
Kranz et al., Nature 313, 752–755 (1985).
Snodgrass et al., Nature 315, 232–233 (1985).
Lefranc and Rabbitts, Nature 316, 464–466 (1985).
Murre et al., Nature 316, 549–552 (1985).
Heilig et al., Nature 317, 68–70 (1985).
Hayday et al., Cell 40, 259–269 (1985).
Dialynas et al., Proc. Natl. Acad. Sci. U.S.A. 83, 2619 (1986).
Iwamoto et al., J. Exp. Med. 163, 1203–1212 (1986).
Zauderer et al., J. Exp. Med. 163, 1314–1318 (1986).
Caccia et al., Cell 37, 1091–1099 (1984).
Kranz et al., Science 227, 941–944 (1985).
Brenner et al., J. Exp. Med. 160, 541–551 (1984).
Spits et al., J. Immunol. 135, 1922–1928 (1985).
Reinherz et al., Cell 30, 735–743 (1982).
Borst et al., J. Biol. Chem. 258, 5135–5141 (1983).
Reinherz et al., Proc. Natl. Acad. Sci. U.S.A. 80, 4104–4108 (1983).
Meuer et al., J. Exp. Med. 157, 705–719 (1983).
Oettgen et al., J. Biol. Chem. 259, 12039–12048 (1984).
Weiss and Stobo, J. Exp. Med. 160, 1284–1299 (1984).
Allison and Lanier, Nature 314, 107–109 (1985).
Brenner et al., Cell 40, 183–190 (1985).
Van den Elsen et al., Proc. Natl. Acad. Sci. U.S.A. 82, 2920–2924 (1985).
Ohashi et al., Nature 316, 606–609 (1985).
Krawinkel et al., Cold Spring Harb. Symp. Quanti. Biol. 4, 285–294 (1976).
Binz and Wigzell, Cold Spring Harb. Symp. Quant. Biol. 4, 275–284 (1976).
Binz and Wigzell, J. Exp. Med. 154, 1261–1278 (1981).
Kung et al., Int. J. Dermat. 22, 67–73 (1983).
Krensky and Clayberger, Transplantation 39(4): 339–348 (1985).
de la Hera et al., Proc. Natl. Acad. Sci. U.S.A. 82, 6268–6271 (1985).
Levin, L. S., et al., J. Pediatrics 90(1), 55–61 (1977).
Griscelli et al., (1980), in Primary Immunodeficiencies, Seligmann, M. and Hitzig, W. H., eds., Elsevier/North-Holland, pp. 499–503.
Hadam, et al., (1984), in Progress in Immunodeficiency Research and Therapy I, Griscelli, C. and Vossen, J., eds., Elsevier Science Publishers B.V., pp. 43–50.
Chan and Takei, J. Immunol. 136(4), 1346–1353 (1986).
Kung et al., U.S. Patent No. 4,614,720, filed Oct. 4, 1982.

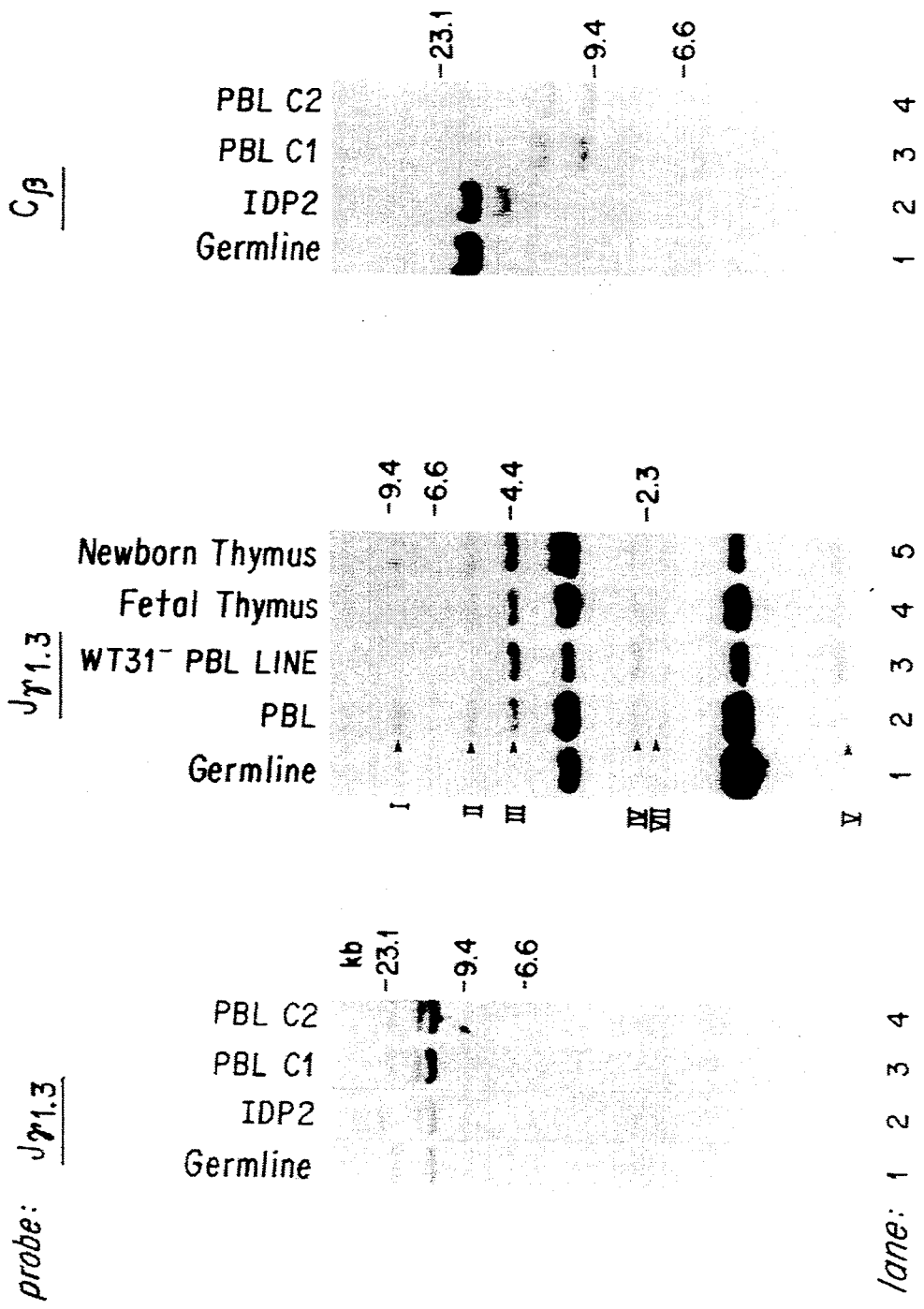

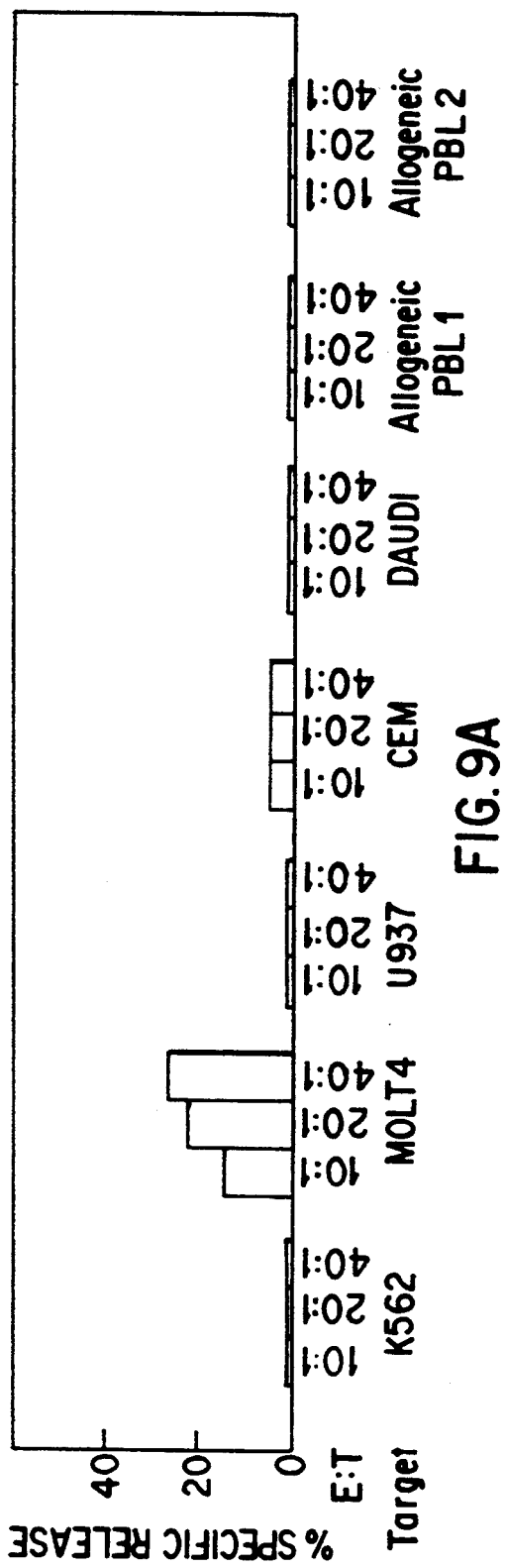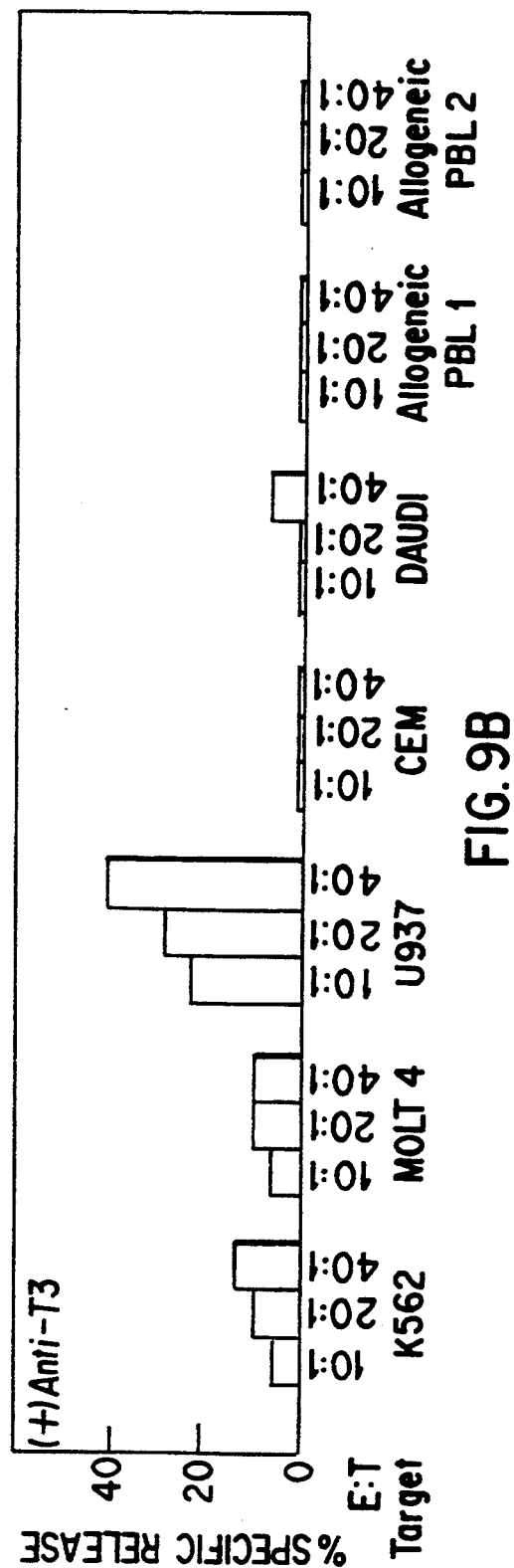

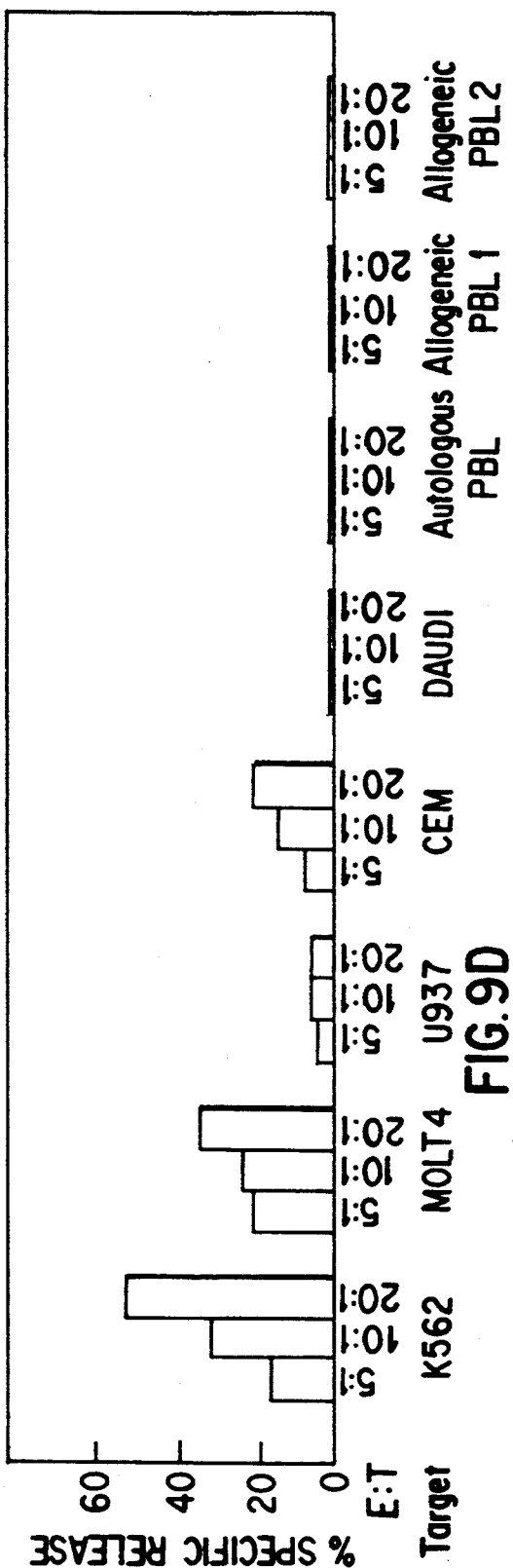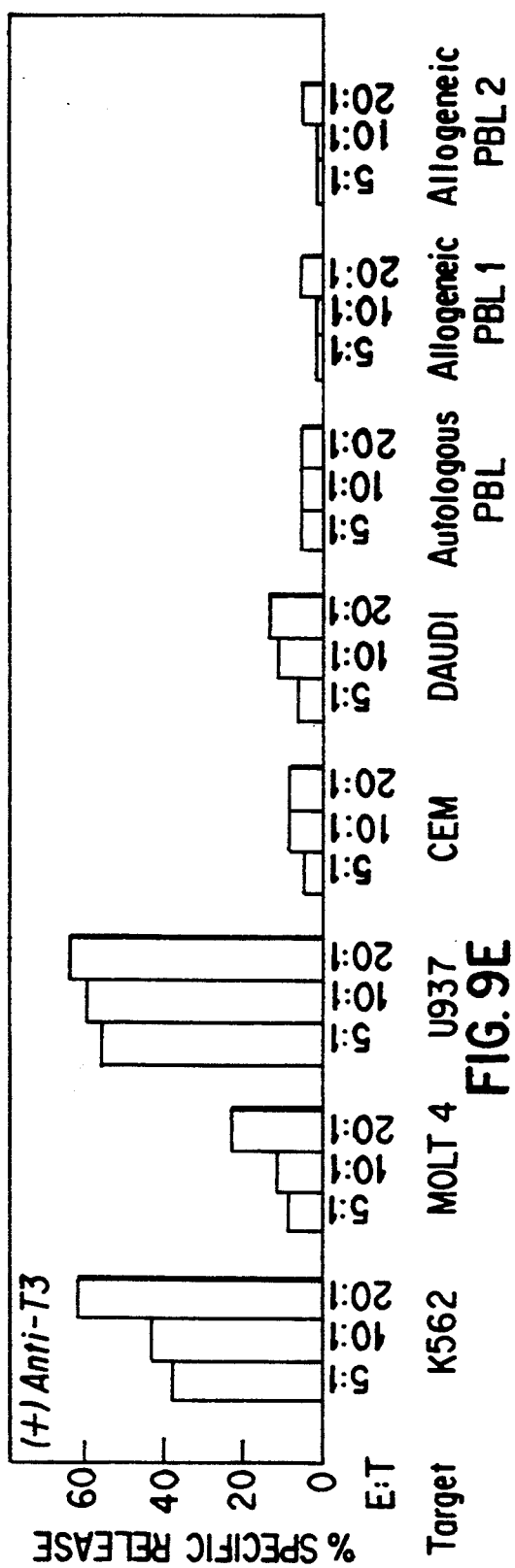

Γ, δT CELL RECEPTOR AND METHODS AND DETECTION

This invention was supported by several NIH grants, and the Government has certain rights to the invention.

This application is a continuation-in-part of U.S. Ser. No. 882,100, filed Jul. 3, 1986, now abandoned, the contents of which are hereby incorporated by reference into the present application.

BACKGROUND OF THE INVENTION

Within this application several publications are referenced by Arabic numerals within parentheses. Full citations for these references may be found at the end of the specification immediately preceding the claims. The disclosures of these publications in their entirety are hereby incorporated by reference into this application in order to more fully describe the state of the art to which this invention pertains.

Understanding T cell recognition of antigen and the restriction of the process by major histocompatibility complex (MHC) encoded antigens has been an important goal in immunology. A major step forward occurred with the immunochemical identification of clone specific disulfide-linked heterodimers on T cells, composed of subunits termed T cell antigen receptors (TCR) α and β. The TCR α and β subunits have a relative molecular mass ($M_r$) of approximately 50,000 and 40,000 daltons, respectively (1, 2, 3). Genes that rearrange during T cell ontogeny and encode the TCR β (4, 5) and TCR α (6, 7, 8) subunits were isolated either by subtractive hybridization or by probing with oligonucleotides.

A unique feature of the human TCR α, β was the observed comodulation (2), coimmunoprecipitation (9, 10) and required coexpression (11) of the TCR α, β molecules with the T3 glycoprotein, which suggested that these two structures were related. Subsequently, the direct physical association of the two protein complexes was demonstrated by chemically cross-linking the TCR α, β molecules to the T3 glycoprotein and identifying the components of the cross-linked complex as the TCR β subunit and the T3 glycoprotein ($M_r$ 28,000) subunit (12). A T3 counterpart is similarly associated with murine TCR α, β (13, 14).

A third gene that rearranges in T cells, designated TCR γ, has been identified in mouse (15, 16, 17) and in man (18, 19). However, there are major differences between the human and mouse TCR gene in terms of its genetic structure; for example, the cDNA of the human TCR γ gene indicates five potential sites for N-linked glycosylation in the TCR γ gene (36) product, which contrasts with the notable absence of such sites in the murine TCR γ gene (15). Thus, the human TCR γ gene product will have a high molecular weight which is not predictable from its genetic sequence.

The TCR γ gene rearrangements occur in lymphocytes with suppressor-cytotoxic as well as helper phenotypes and may produce a large number of TCR γ chains (18, 19, 20, 21, 22, 23). However, the function of the TCR γ gene is unknown. Furthermore, neither the protein encoded by the TCR γ gene nor its possible association with other structures (as occurs with TCR α, β and T3 glycoproteins) have been defined. In humans, the multiple glycosylation sites render it impossible to predict with accuracy the nature and size of the TCR γ polypeptide structure. Additionally, the published literature does not teach or suggest the utility of TCR γ with regard to diagnosing, monitoring or staging human diseases.

It appears increasingly likely that the TCR α, β molecule alone determines both antigen recognition and MHC restriction on at least some T cells (24, 25). However, it is not clear that TCR α, β accounts for the process of T cell selection during T cell ontogeny or for all antigen specific recognition by mature T cells. For example, suppressor T lymphocytes remain an enigma; in some cases they delete or fail to rearrange TCR β genes (26,27). Thus, it is of great importance to determine if a second T cell receptor exists, to define its structure (particularly with regard to the possible use of the TCR γ gene product) and ultimately to understand what function or functions it serves.

SUMMARY OF THE INVENTION

The present invention provides a purified polypeptide which comprises at least a portion of a δT cell receptor polypeptide. Additionally, a substance capable of specifically forming a complex with at least one δT cell receptor polypeptide is provided.

Also provided is a method for detecting T cells, each of which has a δT cell receptor polypeptide. This method comprises contacting a sample which contains T cells with substances capable of forming complexes with δT cell receptor polypeptides so as to form cellular complexes between the substances and the γT cell receptor polypaptides. These cellular complexes are detected and thereby T cells, each of which has a δT cell receptor polypeptide, are detected.

The invention further provides a method for diagnosing an immune system abnormality in a subject. This method comprises determining the number of T cells in a sample from the subject and contacting the sample with substances capable of forming complexes with at least one δT cell receptor polypeptide so as to form cellular complexes between the substances and the δT cell receptor polypeptides. The percentage of T cells in the sample which have a δT cell receptor polypeptide is determined and compared with the percentage of T cells which have a δT cell receptor polypeptide in a sample from a normal subject who does not have the immune system abnormality. A difference in the percentage of T cells so determined would be indicative of the immune system abnormality.

A further method for diagnosing an immune system abnormality in a subject is provided by the present invention. This method comprises determining the number of γT cell receptor polypeptide bearing T cells in a sample from the subject and determining the amount of δT cell receptor polypaptides in the δT cell receptor bearing T cells. The amount of δT cell receptor polypeptides so determined is compared with the amount of δT cell receptor polypeptides in an equal number of δT cell receptor polypeptide bearing T cells in a sample from a normal subject who does not have the immune system abnormality. A difference in the amount so determined would be indicative of the immune system abnormality.

A further method for diagnosing an immune system abnormality in a subject is provided. This method comprises determining in a sample from the subject the number of T cells which have a δT cell receptor polypeptide and the number of T cells consisting of the group of T cells which have one of the surface markers T4, T8 and α, βT cell receptor. The numbers of T cells so determined are compared with the number of T cells which have a δT cell receptor polypeptide and the number of T cells in the group which have the same surface marker as the group of T cells determined in the sample from the subject, in a sample from a subject who does not have the immune system abnormality. A difference in the number of T cells so determined which have a δT cell receptor polypeptide relative to the number of T cells in the group so determined would be indicative of the immune system abnormality.

The present invention also provides a purified polypeptide which comprises at least a portion of a T cell receptor polypeptide. Additionally, a substance capable of specifically forming a complex with at least one γT cell receptor polypeptide is provided. Furthermore, a method for detecting T cells, each of which has a γT cell receptor polypeptide is provided. This method comprises contacting a sample which contains T cells with substances capable of forming complexes with γT cell receptor polypeptides so as to form cellular complexes between the substances and the γT cell receptor polypeptides. These cellular complexes are detected and thereby T cells, each of which has a γT cell receptor polypeptide, are detected.

A further method for diagnosing an immune system abnormality in a subject is provided by the present invention. This method comprises determining the number of T cells in a sample from the subject and contacting the sample with substances capable of forming complexes with at least one γT cell receptor polypeptide so as to form cellular complexes between the substances and the γT cell receptor polypeptides. The percentage of T cells in the sample which have a γT cell receptor polypeptide is determined and compared with the percentage of T cells which have a γT cell receptor polypeptide in a sample from a normal subject who does not have the immune system abnormality. A difference in the percentage of T cells so determined would be indicative of the immune system abnormality.

Still another method for diagnosing an immune system abnormality is provided. This method comprises determining the number of γT cell receptor polypeptide bearing T cells in a sample from the subject and the amount of γT cell receptor polypeptides in the γT cell receptor polypeptide bearing T cells. The amount of γT cell receptor polypeptides so determined is compared with the amount of γT cell receptor polypeptides in an equal number of γT cell receptor polypeptide bearing T cells in a sample from a normal subject who does not have the immune system abnormality. A difference in the amount so determined would be indicative of the immune system abnormality.

Yet another method is provided by the present invention for diagnosing an immune system abnormality in a subject. This method comprises determining in a sample from the subject the number of T cells which have a γT cell receptor polypeptide and the number of T cells consisting of the group of T cells which have one of the surface markers T4, T8 and α, βT cell receptor. The numbers of T- cells so determined are compared with the number of T cells which have a γT cell receptor polypeptide and the number of T cells in the group which have the same surface marker as the group of T cells determined in the sample from the subject, in a sample from a subject who does not have the immune system abnormality. A difference in the number of T cells so determined which have a γT cell receptor polypeptide relative to the number of T cells in the group so determined would be indicative of the immune system abnormality.

The invention further provides a purified complex which comprises at least a portion of a δT cell receptor polypeptide and at least a portion of a δT cell receptor polypeptide. Also provided are substances capable of specifically forming a complex with at least one γ, δT cell receptor complex. Moreover, a method for detecting T cells, each of which has a γ, δT cell receptor complex, is provided. This method comprises contacting a sample which contains T cells with substances capable of forming complexes with γ, δT cell receptor complexes so as to form cellular complexes between the substances and the γ, δT cell receptor complexes. These cellular complexes are detected and thereby T cells, each of which has a γ, δT cell receptor complex, are detected.

Still further, the present invention provides another method for diagnosing an immune system abnormality in a subject. This method comprises determining the number of T cells in a sample from the subject and contacting the sample with substances capable of forming complexes with at least one γ, δT cell receptor complex so as to form cellular complexes between the substances and the γ, δT cell receptor complexes. The percentage of T cells which have a γ, δT cell receptor complex is determined and compared with the percentage of T cells which have a γ, δT cell receptor complex in a sample from a normal subject who does not have the immune system abnormality. A difference in the percentage of T cells so determined would be indicative of the immune system abnormality.

The invention provides yet another method of diagnosing an immune system abnormality in a subject. This method comprises determining the number of γ, δT cell receptor complex bearing T cells in a sample from the subject and the amount of γ, δT cell receptor complexes in the γ, δT cell receptor complex bearing T cells. The amount of γ, δT cell receptor complexes so determined is compared with the amount of γ, δT cell receptor complexes in an equal number of γ, δT cell receptor complex bearing T cells in a normal subject who does not have the immune system abnormality. A difference in the amount so determined would be indicative of the immune system abnormality.

Yet another method for diagnosing an immune system abnormality is provided by the present invention. This method comprises determining in a sample from the subject the number of T cells which have a γ, δT cell receptor complex and the number of T cells consisting of the group which have one of the surface markers T4, T8 and α, βT cell receptor complex. The numbers of T cells so determined are compared with the number of T cells which have a γ, δT cell receptor complex and the number of T cell s in the group which have the same surface marker as the group of T cells determined in the sample from the subject, in a sample from a subject who does not have the immune system abnormality. A difference in the number of T cells so determined which have a γ, δT cell receptor complex relative to the number of T cells in the group would be indicative of the immune system abnormality.

Figure 1A:
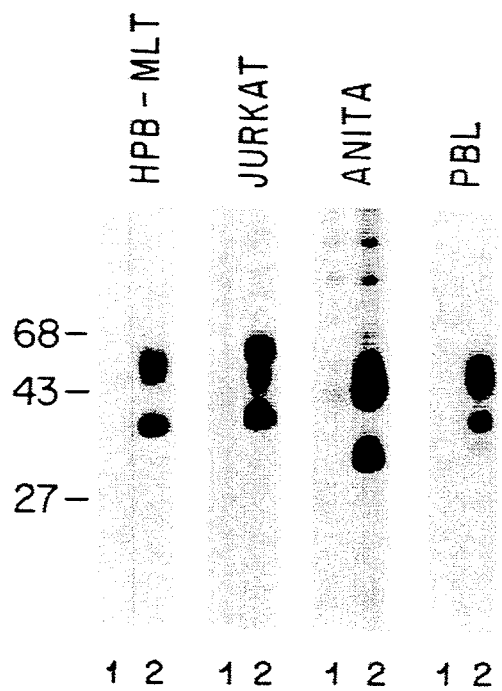
FIG. 1 Reactivity of framework monoclonal antibodies recognizing TCR, α, β.
A.
Lane 1: Control antibody, normal mouse serum.

Lane 2: Anti-framework TCR α, β monoclonal antibody (βF1).

B.
Lane 1: Control antibody, normal mouse serum.
Lane 2: Anti-T3 monoclonal antibody (UCH T-1).
Lane 3: Anti-framework TCR, monoclonal antibody (WT31).

C. Three dimensional display of flow cytometry analysis of normal adult peripheral blood lymphocytes. Red and green fluorescence were measured and compared to non-specific control FITC- and biotin- conjugated monoclonal antibodies. Cells unreactive with either monoclonal antibody were non T cells (lower left corner); cells that were double positive, i.e. reacting with both OKT·3 and βF1, make up the large population of lymphocytes in the center region of the grid; cells that were F1− but OKT·3+ comprise a small but distinct group of lymphocytes (4% of the T3+ cells) observed along the X-axis.

FIG. 2 SDS-PAGE analysis of cell surface T3 and T3-associated (cross-linked) molecules by immunoprecipitation from IDP1 and IDP2 cell lines.

IDP1 cell line 2 (WT31+) and cell line 3 (WT31−).
Lanes 1, 2, 7, 8: Normal mouse serum.
Lanes 3, 4, 9, 10: Anti-T3 monoclonal antibody (UCHT-1).
Lanes 5, 6, 11, 12: Anti-framework TCR α, β monoclonal antibody (βF1).

IDP2 cell line 7 (88% WT31−T3+)
Lanes 1, 4, 7, 10: Normal mouse serum.
Lanes 2, 5, 8, 11: Anti-framework TCR monoclonal antibody (βF1).
Lanes 3, 6, 9, 12: Anti-T3 monoclonal antibody (UCHT-1).
$^{125}$I-labeled samples XL-cross-linked with DSP.

IDP2 cell line 5 (WT31+T3+) and cell line 7 (88% WT31−T3+).
Lanes 1, 3: Normal mouse serum.
Lanes 2, 4: Anti-T3 monoclonal antibody (UCHT-1).

FIG. 3 Northern blot analysis of RNA isolated from IDP2 cell lines using TCR, TCR β and TCR γ cDNA probes.
A.
Lane 1: IDP2 cell line (WT31−).
Lane 2: T leukemic cell line HBP-MLT.
B.
Lane 1: IDP2 cell line 5 (WT31+T3+).
Lane 2: IDP2 cell line 7 (88% WT31−T3+).
Lane 3: Cell line HPB-MLT.

FIG. 4 Anti-V γ and anti-C γ peptide sera immunoprecipitations from IDP2 cell line 7.
A.
Lane 1: Normal mouse serum.
Lane 2: Anti-V γ peptide mouse serum.
Lane 3: Normal rabbit serum.
Lane 4: Anti-C γ peptide rabbit serum.
B.
Lane 1: Normal mouse serum.
Lane 2: Anti-T3 monoclonal antibody (UCHT-1).
Lane 3: Normal rabbit serum.
Lane 4, 5: Anti-C γ peptide rabbit serum.

FIG. 5 Immunoprecipitations of TCR γ,δ and T3 from a human tumour and peripheral blood lymphocyte lines.
Immunoprecipitations from $^{125}$I-labelled cell lysates were analysed by SDS-PAGE (10% acrylamide) under reducing (R) or nonreducing (N or NR) conditions. Size markers, M$_r$ in thousands.

TCR γ, δ and T3 subunits on IDP2 and PEER cells. Immunoprecipitations were performed using 1 μg control mAb P3 (mAb secreted by the P3X63.Ag8 myeloma lanes 1, 3, 5 and 6): 1 μg UCHT1 (anti-T3) (40) (lanes 2, 4, 7 and 8); 10 μl normal rabbit serum (NRS lane 9) and 10 μl anti-Cγ peptide sera (anti-TCR γ) (lane 10). Arrows indicate positions of TCR δ subunits which change mobility under R and NR conditions.

TCR γ,δ and T3 subunit on peripheral blood T cell clone, PBL C1 and the WT31−PBL LINE. Immunoprecipitations were performed using control mAb P3 (lanes 1, 4, 9 and 12), 1 μg βF1 (anti-TCRβ) (lanes 2,5, 10 and 13). NRS (lanes 7 and 15) and anti-C γ peptide sera (lanes 8 and 16). Open arrow indicates disulphide-linked βF1 and unreactive T3-associated species; solid arrow indicates non-disulphide-linked, T3-associated material that displays increased SDS-PAGE mobility under nonreducing conditions (like TCR δ in A).

Figure 6:
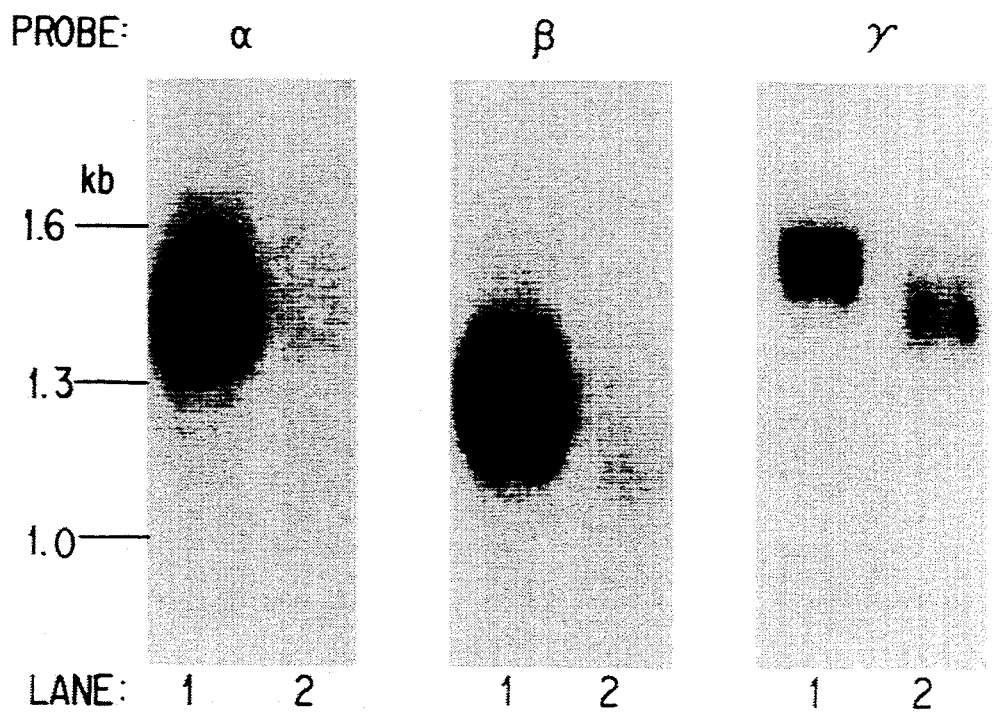

FIG. 6
Northern blot analysis of RNA isolated from PBL C1.
Total RNA preparations from the T leukaemic cell line HPB-MLT (lane 1 for each probe and PBL C1 (lane for each probe) were analysed on Northern Blots using TCRα, TCRβ and TCR γ cDNA probes.

FIG. 7
Two-dimensional gel analysis of TCR γ polypeptides and precursors.

Panels A–D Comparison of reduced (separated) and nonreduced (dimeric) T3-associated polypeptides from PBL C1 cells were lysed in CHAPS and immunoprecipitated with anti-T3 mAb. Two-dimensional gel electrophoresis was carried out under reducing conditions (A,C) or nonreducing conditions (B,D). The T3γ, δ and ε positions are labelled and focused to similar positions under both R and N conditions. After cleaving the disulphide bond, the T3 associated polypeptides (40K and 36K) migrated to focusing positions close to T3γ R conditions, but shifted to a more acidic position (close to T3δ) under N conditions (when both components of the dimer were present (68K). Size markers, M$_r$.

Panels E–H Analysis of glycosylated and non-glycosylated IDP2 and PBL C1 TCR γ peptide precursors. IDP2 and PBL C1 cells were pulse-labelled with $^{35}$S-methionine, lysed under denaturing conditions and immunoprecipitated with anti-C γ peptide sera. Immunoprecipitations were then either treated and with endo-H or mock treated and analysed by two-dimensional gel electrophoresis. Glycosylated TCR γ peptides are denoted by open arrows, and non-glycosylated TCR γ peptides by solid arrows. Apparent relative molecular masses were calculated from migration of standards used in panels A and B (not shown). A small amount of contaminating actin, denoted by a diamond in each panel, served as an internal marker. E, IDP2 TCR γ, mock incubated; F, IDP2 TCR γ, endo H treated; G, PBL C1 TCR γ mock incubated; H, PBL C1 TCR γ endo-H treated.

FIGS. 8A, 8B, 8C
Rearrangement of the γ and β genes in T cells expressing the TCR γ polypeptide.
Genomic DNAs isolated from the IDP2 cell line, PBL C1, PBL C2, WT31− PBL LINE, fetal thymus, newborn thymus, PBL and a B cell line (JY for germline) were examined in Southern blot analysis for TCR γ (A, B) and TCR β (C) gene rearrangements. Genomic DNAs were digested with BamHI (A, C) or EcoRI (B) fractionated on agarose gels and transferred to nitrocellulose filters for hybridization with $^{32}$p-labelled J$_{\gamma 1,3}$ (A,B) or C2 probes (C). Arrows and roman numerals denote TCR $\gamma$ rearrangements. Size markers in kb.

FIG. 9 Cytolysis by IDP2 and PBL C1 cells.

Panels A, B, D, E IDP2 or PBL C1 effector cells were incubated (at effector:target, (E:T) ratios indicated) with $^{51}$Cr-labelled target cells K562 (erythroid line), U937 (monocytic line), MOLT-4, CEM (T leukaemic lines), Daudi (Burkitt's lymphoma line) or allogeneic or autologous PBL (3-day PHA blasts of human PBL). Panels A and D: The % specific release of $^{51}$Cr for each target is shown. Panels B and E: The same assays were carried out after prebinding anti-T3 mAb UCHT1 to the reactor cells for 30 minutes at 0° C. (+anti-T3).

Panel Inhibition of IDP2 cytolysis of MOLT-4 target cells by various mAb. IDP2 and $^{51}$Cr-labelled MOLT-4 cells were incubated together at a 40:1 E:T ratio in the presence of various dilutions of anti-MHC Class 1 mAb W6/32 (anti-HLA-A, B, C monomorphic determinant) (58), anti-HLA A, B, C (monomorphic determinant) (59), 4E (anti-HLA-B and C locus) (60), 131 (anti-HLA-A locus) (61) or anti-MHC Class II mAb LB3.1 (anti-DR specific) (62), anti-Leu 10 (anti-DQ specific) (63) or anti-T3 mAb UCHT1. Higher dilutions were used for mAb as ascites (W6/32, 4E, 131, LB3.1 and UCHT1) and lower dilutions were used for commerical mAb (anti-Leu 10) or culture supernatant (anti-HLA-A, B, C).

DETAILED DESCRIPTION OF THE INVENTION

The present invention provides a purified polypeptide which comprises at least a portion of a $\delta$T cell receptor polypeptide. This polypeptide may have at least one intrachain, covalent, disulphide bridge. Additionally, the polypeptide may comprise a $\gamma$T cell receptor polypeptide having a molecular weight of about 40,000 daltons. Furthermore, the $\gamma$T cell receptor polypeptide may be a human $\delta$T cell receptor polypeptide.

A substance capable of specifically forming a complex with at least one $\delta$T cell receptor polypeptide is also provided by the invention. In one embodiment of the invention, the substance is capable of specifically forming a complex with one $\delta$T cell receptor polypeptide. In another embodiment of the invention, the substance is capable of specifically forming a complex with more than one $\delta$T cell receptor polypeptide. The substance may be an antibody. The antibody may be a polyclonal antibody or a monoclonal anti body.

Also provided is a method for detecting T cells, each of which has a $\delta$T cell receptor polypeptide. This method comprises contacting a sample containing T cells with substances capable of forming complexes with $\gamma$T cell receptor polypeptides so as to form cellular complexes between the substances and the $\delta$T cell receptor polypeptides. These cellular complexes are detected and thereby T cells, each of which has a $\delta$T cell receptor polypeptide, are detected.

Accordingly, in one embodiment of the invention, the $\delta$T cell receptor polypeptides are present on the surfaces on the T cells. In another embodiment of the invention, the $\delta$T cell receptor polypeptides are present in the cytoplasm of the T cells.

This method may be performed by forming complexes with a specific $\delta$T cell receptor polypeptide. In one embodiment of the invention, the specific $\delta$T cell receptor polypeptide is present only in suppressor T cells.

The invention further provides a method for diagnosing an immune system abnormality in a subject. Within this application, immune system abnormality means a condition of immunological responsiveness to antigens characterized by an increased or a decreased immune response compared to a normal or standard immune response. Accordingly, immune system abnormality includes, but is not limited to, immunodeficiency conditions and diseases, e.g. acquired immune deficiency syndrome and congenital immunodeficiencies and hyperimmune conditions and diseases, e.g. allergies and hayfever. The method of the present invention comprises determining the number of T cells in a sample from the subject and contacting the sample with the substances capable of forming complexes with at least one $\delta$T cell receptor polypeptide so as to form cellular complexes between the substances and $\delta$T cell receptor polypeptides. The percentage of T cells in the sample which have a $\delta$T cell receptor polypeptide is determined and compared with the percentage of T cells which have a $\delta$T cell receptor polypeptide i a sample from a normal subject who does not have the immune system abnormality. A difference in the percentage of T cells so determined would be Indicative of the immune system abnormality.

In one embodiment of the invention, the immune system abnormality is a cancer. The cancer may be a leukemia or a lymphoma. In another embodiment of the invention, the immune system abnormality is acquired immune deficiency syndrome. In yet another embodiment of the invention, the immune system abnormality is congenital immunodeficiency. In still a further embodiment of the invention, the immune system abnormality is an autoimmune disease.

The subject in whom the immune system abnormality is diagnosed may be an animal. In one embodiment of the invention the subject is a human. Furthermore, the sample from the subject may comprise blood or tissue.

Yet another method for diagnosing an immune system abnormality is provided by the present invent/on. This method comprises determining the number of $\delta$T cell receptor polypeptide bearing T cells in a sample from the subject and the amount of $\delta$T cell receptor polypeptides in the T cell receptor polypeptide bearing T cells. The amount of $\delta$T cell receptor polypeptides so determined is compared with the amount of $\delta$T cell receptor polypeptides in an equal number of $\delta$T cell receptor polypeptide bearing T cells in a sample rom a normal subject who Goes not have the immune system abnormality. A difference in the amount so determined would be indicative of the immune system abnormality. In one embodiment of the invention, the amount of a single $\delta$T cell receptor polypeptide is determined.

A further method for diagnosing an immune system abnormality in a subject is provided. This method comprises determining in a sample from the subject the number of T cells which have a $\delta$T cell receptor polypeptide and the number of T cells consisting of the group of T cells which have one of the surface markers T4, T8 and $\alpha$, $\beta$T cell receptor. The numbers of T cells so determined is compared with the number of T cells which have a $\delta$T cell receptor polypeptide and the number of T cells in the group which have the same surface marker as the group of T cells determined in the sample from the subject, in a sample from a subject who does not have the immune system abnormality. A difference in the number of T cells so determined which have a δT cell receptor polypeptide relative to the number of T cells in the group so determined would be indicative of the immune system abnormality.

The present invention also provides a nucleic acid molecule encoding a δT cell receptor polypeptide having a molecular weight of about 40,000 daltons. In one embodiment of the invention, the molecule is a DNA molecule. Further provided is a nucleic acid molecule which is complementary to the nucleic acid molecule which encodes a δT cell receptor polypeptide.

A purified polypeptide which comprises at least a portion of a γT cell receptor polypeptide is also provided by the present invention. This polypeptide may comprise a γT cell receptor polypeptide having a molecular weight of about 55,000 daltons. In one embodiment of the invention, the polypeptide has a peptide sequence with a molecular weight within the range from about 31,000 daltons to about 40,000 daltons. Additionally, the polypeptide may be a human γT cell receptor polypeptide.

The present invention further provides a purified complex which comprises two γT cell receptor polypeptides of the present invention associated with each other. In one embodiment of the invention, the two γT cell receptor polypeptides are associated with each other through at least one interchain, covalent, disulphide linkage. In another embodiment of the invention, the two γT cell receptor polypeptides are noncovalently associated with each other. In still another embodiment of the invention, the two γT cell receptor polypeptides have the same constant domain. In yet a further embodiment of the invention, the two γ T cell receptor polypeptides have different constant domains.

The present invention also provides a substance capable of specifically forming a complex with at least one γT cell receptor polypeptide. In one embodiment of the invention, the substance is capable of specifically forming a complex with one γT cell receptor polypeptide. In another embodiment of the invention, the substance is capable of specifically forming a complex with more than one γT cell receptor polypeptide. The substance may be an antibody. In one embodiment of the invention, the antibody is a polyclonal antibody. In another embodiment of the invention, the antibody is a monoclonal antibody.

A method for detecting T cells, each of which has a γT cell receptor polypeptide, is further provided. This method comprises contacting a sample which contains T cells with substances capable of forming complexes with γT cell receptor polypeptides so as to form cellular complexes between the substances and the γT cell receptor polypeptides. These cellular complexes are detected and thereby T cells, each of which has a γT cell receptor polypeptide, are detected. In one embodiment of the invention, the γT cell receptor polypeptides are present on the surfaces of the T cells. In another embodiment of the invention, the γT cell receptor polypeptides are present in the cytoplasm of the T cells. In yet another embodiment of the invention, the substances are capable of forming complexes with a specific γT cell polypeptide. The specific γT cell receptor polypeptide may be present only in suppressor T cells. Furthermore, the γT cell receptor polypeptide may be associated with another γT cell receptor polypeptide.

In one embodiment of the invention, the γT cell receptor polypeptide is associated with another γT cell receptor polypeptide. In another embodiment of the invention, the γT cell receptor polypeptide is associated with another γT cell receptor polypeptide only in non-major histocompatibility restricted cytotoxic T lymphocytes. Furthermore, the non-major histocompatibility complex restricted cytotoxic T lymphocytes may be T killer cells or natural killer-like cells.

The present invention further provides a method for diagnosing an immune system abnormality in a subject. This method comprises determining the number of T cells in a sample from the subject and contacting the sample with substances capable of forming complexes with at least one γT cell receptor polypeptide so as to form cellular complexes between the substances and γT cell receptor polypeptides. The percentage of T cells in the sample which have a γT cell receptor polypeptide is determined and compared with the percentage of T cells which nave a γT cell receptor polypeptide in a normal subject who does not nave the immune system abnormality. A difference in the percentage of T cells so determined would be indicative of the immune system abnormality. In one embodiment of the invention, the immune system abnormality is a cancer. The cancer may be a leukemia or a lymphoma. In another embodiment of the invention, the immune system abnormality is acquired immune deficiency syndrome. In yet another embodiment of the invention, the immune system abnormality is congenital immunodeficiency. In still a further embodiment of the invention, the immune system abnormality is an autoimmune disease.

The subject in which the immune system abnormality is diagnosed may be an animal. Additionally, the subject in which the immune system abnormality is diagnosed may be a human. Furthermore, the sample of which the percentage of T cells which have a γT cell receptor polypeptide is determined may comprise blood or tissue.

Yet another method tot diagnosing an immune system abnormality in a subject is provided by the present invention. This method comprises determining the number of γT cell receptor polypeptide bearing T cells in a sample t tom the subject and the amount of γT cell receptor polypeptides in the γT cell receptor polypeptide bearing T cells. The amount of γT cell receptor polypeptides so determined is compared with the amount of γT cell receptor polypeptides in an equal number of γT cell receptor polypeptide bearing T cells in a sample from a normal subject who does not have the immune system abnormality. A difference in the amount so determined would De Indicative of the immune system abnormality. In one embodiment of the invention, the amount of a single γT cell receptor polypeptide is determined.

Further provided is another method for diagnosing an immune system abnormality in a subject. This method comprises determining in a sample from the subject the number of T cells which have a γT cell receptor polypeptide and the number of T cells consisting of the group of T cells which have one of the surface markers T4, T8 and, 8 T cell receptor. The numbers of T cells so determined are compared with the number of T cells which have a γT cell receptor polypeptide and the number of T cells in the group which have the same surface marker as the group determined in the sample from the subject, in a sample from a subject who does not have the immune system abnormality.

A difference in the number of T cells so determined which have a γ T cell receptor polypeptide relative to the number of T cells in the group so determined would be indicative of the immune system abnormality.

A purified complex which comprises at least a portion of a δT cell receptor polypeptide and at least a portion of a γT cell receptor polypeptide is further provided by the present invention. This complex may comprise a δT cell receptor polypeptide having a molecular weight of about 40,000 daltons and a γT cell receptor polypeptide having a molecular weight of about 55,000 daltons. Furthermore, the γT cell receptor polypeptide may be a human δT cell receptor polypeptide and the γT cell receptor polypeptide may be a human γ T cell receptor polypeptide. Moreover, the δT cell receptor polypeptide and the γT cell receptor polypeptide may be associated with each other through at least one interchain, covalent, disulphide linkage, or may be noncovalently associated with each other.

Also provided is a substance capable o specifically forming a complex with at least one γ, δT cell receptor complex. This substance may be capable of forming a complex with one γ, δT cell receptor complex. Furthermore, the substance may be capable of forming a complex with more than one γ, δT cell receptor complex.

In one embodiment of the invention, the substance is an antibody. In another embodiment of the invention, the substance is a polyclonal antibody. In yet another embodiment of the invention, the substance is a monoclonal antibody.

The present invention further provides a method for detecting T cells, each of which has a γ, δT cell receptor complex. This method comprises contacting a sample containing T cells with substances capable of forming complexes with γ, δT cell receptor complexes so as to form cellular complexes between the substances and the γ, δT cell receptor complexes. These cellular complexes are detected and thereby T cells, each of which has a γ, δT cell receptor complex, are detected. In one embodiment of the invention, the γ, δT cell receptor complexes are present on the surface of the T cells. In another embodiment of the invention, the γ, δT cell receptor complexes are present in the cytoplasm of the T cells. In yet another embodiment of the invention, the substances are capable of forming complexes with a specific γ, δT cell receptor complex. The specific γ, δT cell receptor complex may be present only in suppressor T cells.

A method for diagnosing an immune system abnormality in a subject is further provided by the present invention. This method comprises determining the number of T cells in a sample tom the subject and contacting the sample with substances capable of forming complexes with at least one γ, δT cell receptor complex so as to form cellular complexes between the substances and γ, δT cell receptor complexes. The percentage of T cells in the sample which have a γ, δT cell receptor complex is determined and compared with the percentage of T cells which have a γ, δT cell receptor complex in a sample from a normal subject who does not have the immune system abnormality. A difference in the percentage of T cells so determined would be indicative of the immune system abnormality. In one embodiment of the invention, the immune system abnormality is a cancer. The cancer may be a leukemia or a lymphoma. In another embodiment of the invention, the immune system abnormality is acquired immune deficiency syndrome. In yet another embodiment of the invention, the immune system abnormality is congenital immunodeficiency. In yet a further embodiment of the invention, the immune system abnormality is an autommune disease.

The subject in which the immune system abnormal ity may be an animal. Furthermore, the subject in which the immune system abnormal ity is diagnosed may be a human. Moreover, the sample in which the percentage of T cells which have a γ, δT cell receptor complex is determined may comprise blood or tissue.

Still another method tot diagnosing an immune system abnormality in a subject is provided by the present invention. This method comprises determining the number of γ, δT cell receptor complex bearing T cells in a sample from the subject and the amount of γ, δT cell receptor complexes in the γ, δT cell receptor complex bearing T cells. The amount so determined is compared with the amount of γ, δT cell receptor complexes in an equal number of γ, δT cell receptor complex bearing T cells in a sample from a normal subject who does not have immune system abnormality. A difference in the amount so determined would be indicative of the immune system abnormality. In one embodiment of the invention, the amount of a single γ, δT cell receptor complex is determined.

Yet a further method for diagnosing an immune system abnormality is provided. This method comprises determining in a sample from the subject the number of T cells which have a γ, δT cell receptor complex and the number of T cells consisting of the group of T cells which have one of the surface markers T4, T8 and α, βT cell receptor. The numbers of T cells so determined are compared with the number of T cells which have a γ, δT cell receptor complex and the number of T cells in the group which have the same surface marker as the group of T cells determined in the sample from the subject, in a sample from a subject who does not have the immune system abnormality. A difference in the number of T cells so determined which have a γ, δT cell receptor complex relative to the number of T cells in the group so determined would be indicative of the immune system abnormality.

The various methods for diagnosing abnormalities and for detecting T cells provided by the present invention are based upon the novel polypeptides and substances capable of forming complexes with these polypeptides as described more fully hereinabove. The methods utilize methods for detecting and quantifying T cells, including but not limited to, fluorescence activated cell sorting and autoradiography, which are well known to those skilled in the art to which this invention pertains.

Materials and Methods

Lymphocyte culture and cell population analysis

Viable lymphocytes were isolated by Ficoll-hypaque density centrifugation and stained with 0.5 micrograms of a specific monoclonal antibody, e.g. WT31 (28, 29) or OKT-3, OKT-4 or OKT-8 (Ortho Diagnostic Systems, Inc., Raritan, N.J.), for 30 minutes at 4° C. After washing, the cell pellets were stained again with fluorescein isothiocyanate (FITC) -conjugated goat antimouse IgF(ab)'$_2$ fragments. Fluorescence activated cell sorter (FACS) analyses were performed on an Ortho cytofluorograph or a Coulter Epics as previously described (37). Specifically stained positive cells were determined relative to a negative control profile for each cell line (stained with a nonspecific control monoclonal antibody). Cells having fluorescence intensity channel numbers greater than the intercept of the negative control profile with the baseline were counted as positive, and the % positive was calculated relative to the total number of cells counted.

All cell lines were propagated in vitro in media composed of RPMI 1640, 10% human serum and conditioned media containing 2-5 units of interleukin-2 activity as previously described (34).

Alloantigen (allo) activated cultures were stimulated with irradiated allogenic peripheral blood lymphocytes at weekly interval s. Mitogen, i.e. phytohemagglutinin (PHA), activated lines were stimulated with a 1:1,000 dilution of PHA (Difco, Detroit, Mich.) at culture initiation.

Reactivity and characterization of cell culture using monoclon antibodies

Immunoprecipitates from $^{125}$I-labeled lymphocyte lysates were analyzed by sodium dodecyl sulfate-polyacrylamide gel electrophoresis (SDS-PAGE). The radioiodinated T leukemia cell lines HPB-MLT and Jurkat, the HTLV-1 transformed cell line ANITA and resting peripheral blood lymphocytes were solubilized in 1% Triton-X-100 (TX-100) and immunoprecipitated with a control antibody, normal mouse serum (NMS) or a framework antibody to TCR $\alpha$, $\beta$ i.e., $\beta$F1 (54). The $\beta$F1 monoclonal antibody was prepared according to standard procedures (47, 52). Spleen cells from mice immunized with purified TCR $\alpha$, $\beta$ as described in (28) were used for the fusion experiments. A positive clone, $\beta$F1, was obtained by immunoprecipitation with T cell lines and peripheral blood lymphocytes as described above.

$^{125}$I-labeled lymphocytes were solubilized in 0.1% TX-100 and immunoprecipitated with NMS, the anti-T3 antibody UCHT-1 (40) and a framework antibody to TCR i.e., WT31. The efficiency of immunoprecipitation with WT31 was improved at the lower TX-100 concentration used here and the monoclonal antibody 187.1 (53) was used as a second antibody.

Two-color FACS analysis of normal adult peripheral blood lymphocytes was performed using an anti-TCR $\alpha$, $\beta$ monoclonal antibody and an anti-T3 monoclonal antibody. Peripheral blood lymphocytes were stained first with an FITC-conj ugated anti-T3 monoclonal antibody (OKT-3) and then with a biotinyl-anti-TCR $\alpha$, $\beta$ monoclonal antibody ($\beta$F1) followed by phycoerythrin-conjugated avidin (PE-avidin, Becton Dickenson, Mr. View, Calif.).

Viable lymphocytes were isolated by ficoll-hypaque density centrifugation for SDS-PAGE and FACS analyses. For SDS-PAGE analysis, lymphocytes were radioiodinated by the lactoperoxidase technique, solubilized in 1% TX-100 and immunoprecipitated using 1 microgram of a specific antibody, i.e. monoclonal antibody SF1 or monoclonal antibody UCHT-1, or 1 microliter of NMS. The immunoprecipitates were then analysed by 10.5% SDS-PAGE under reducing conditions. The $^{125}$I-labeled molecules were visualized by autoradiography as previously described (28).

Two-colored cytofluorographic analysis was performed by first staining with FITC-OKT-3 monoclonal antibody for 45 minutes at 4° C. After washing, the lymphocytes were fixed in 1% paraformaldehyde for 15 minutes at 23° C. then incubated in 70% ethanolin phosphate buffered saline (PBS) for 5 minutes at −20° C. After further washing, the cells were stained with the biotinyl-$\beta$F1 monoclonal antibody followed by PE-avidin. Analysis was performed on an Ortho ® cytofluorograph (Ortho Diagnostic Systems, Inc., Westwood, Mass.).

Analysis of cell surface protein molecules associated with T3 molecules on IDP1 and IDP2 cell lines IDP1 cell line 2 (WT31+) and cell line 3 (WT31−) were $^{125}$I-labeled as described above. Radioiodinated, intact lymphocytes were then either cross-linked by incubation in PBS (pH 8) containing 50 micrograms/ml di-thio-bis-succinimidyl propionate (DSP) or mock incubated. The cells were then solublized in 1% TX-100 and immunoprecipitated as previously described (12). T3 associated molecules ($M_r$ 40,000–55,000) in the anti-T3 immunoprecipitations were detected at low levels in the noncross-linked samples and at higher levels in the cross-linked samples.

IDP2 cell line 7 ( 88% WT31−T3+) was $^{125}$I-labeled and treated with DSP or mock incubated. Immunoprecipitations were performed using NMS, the anti-T3 monoclonal antibody UCHT-1 and the anti-TCR $\alpha$, $\beta$ monoclonal antibody $\beta$F1 either without or with preclearing TCR $\alpha$, $\beta$ molecules with the monoclonal antibody $\beta$F1. A small fraction of radiolabeled TCR $\alpha$, $\beta$ was detected in samples which were not precleared but not in samples which were precleared with $\beta$F1.

IDP2 cell line 5 (WT31+T3+) and cell line 7 (88% WT31−T3+) were $^{125}$I-labeled, solubilized in 1% TX-100 and immunoprecipitated using NMS or the anti-T3 monoclonal antibody UCHT-1. The T3 heavy subunit ($M_r$ 27,000) appeared similar on these two cell lines, while the T3 light subunits ($M_r$ 19,000–25,000) did not.

$^{125}$I-labeling, solubilization in 1% TX-100, immunoprecipitation and visualization after 10.5% SDS-PAGE analysis by autoradiography were performed as previously described (28). Chemical cross-linking was performed for 30 minutes at 23° C. on intact radiolabeled lymphocytes using DSP (50 micrograms/ml) in PBS (pH 8) as previously described (12). After immunoprecipitation, all samples were examined by SDS-PAGE under reducing conditions using 5% 2-mercaptoethanol, which cleaved both the disulfide bonds between protein subunits and the DSP chemical cross-link.

Northern blot analysis of RNA isolated from IDP2 cell lines using TCR$\alpha$, TCR$\beta$ and TCR$\gamma$ cDNA probes Total RNA (15 micrograms) isolated from IDP2 cell line 6 (WT31−) and from T leukemic cell line HBP-MLT was fractionated on a 1.5% agarose gel containing 2.2M formaldehyde, transferred to nitrocellulose and hybridized with TCR $\alpha$, TCR $\beta$ and TCR $\gamma$ probes. Total RNA (3 micrograms) isolated from IDP2 cell line 5 (WT31−T3+), IDP2 cell line 7 (88% WT31−T3+) and HPB-MLT was analyzed as described above.

RNA preparation, electrophoresis, transfer to nitrocellulose and hybridization with $^{32}$p-labeled, nick-translated probes (1–3×10$^8$ cpm/microgram) were as described previously (41). $\alpha$-chain probes were either the human cDNA clones pGA5 (8) or L17 $\alpha$ (42). $\beta$chain probes were either the human cDNA clones 12A1 (43) or L17 (43). The $\gamma$-chain probe was an EcoRI to AccI fragment derived from human cDNA clone T$\gamma$-1 (36). Radioactive bands were visualized by autoradiography using intensifying screens. All probes were labeled to nearly identical specific activity, and identical exposure times are presented.

Immunoprecipitation of IDP2 cell line 7 surface molecules usinq anti-$\gamma$ antiserum TX-100 solubilized $^{125}$I-labeled IDP2 cell line 7 (88% WT31$^-$T3$^+$) was denatured (see below) and then immunoprecipitated with NMS or normal rabbit serum and with anti-V γ peptide serum or anti-Cγ peptide serum. A specific band was observed at $M_r$ 55,000 in both the anti-V γ and anti-Cγ immunoprecipitations. The additional band at $M_r$ 90,000 was not reproducibly observed in the anti-Cγ immunoprecipitations (see below). DSP cross-linked native lysates (1% TX-100) from $^{125}$I-labeled IDP2 cell line 7 were immunoprecipitated with NMS or with the anti-T3 monoclonal antibody UCHT-1. Alternatively, the lysate was denatured (as described below) and immunoprecipitated with either normal rabbit serum or with anti-C Y peptide serum.

An additional aliquot of lysate was subjected to a two stage immunoprecipitation. Polypeptides were immunoprecipitated with the anti-T3 monoclonal antibody UCHT-1, and were eluted from the immunoabsorbent under denaturing and reducing conditions, in order to break the DSP cross-link. Immunoprecipitation from this eluate was then performed using anti-Cγ peptide serum.

$^{125}$I-labeling, solubilization in 1% TX-100 and immunoprecipitation were performed as described above. Native lysates (1% TX-100) were denatured by the addition of SDS (final concentration of 1%) and dithiothreitol (final concentration of 2 mM) followed by heating the mixture for 5 minutes at 68° C. After cooling, iodoacetamide was added (20 mM final concentration) and samples were diluted with the addition of 4 volumes of 1.5 26% TX-100 in Tris buffered saline (pH 8). The initial immunoprecipitate in the experiment was denatured and subsequently partially renatured (28). Samples were immunoprecipitated with 10 microliters of anti-C γ or anti-V γ peptide sera, 1 microgram of UCHT-1 or 1 microliter of NMS or normal rabbit serum and analyzed by 10.5% SDS-PAGE under reducing conditions (5% 2-mercaptoethanol).

Peptides corresponding to deduced V γ or C γ amino acid sequences (residue numbers noted below in the Experimental Result section) were synthesized on a Beckman 990 peptide synthesizer using the method of Erickson and Merrifield (44). Peptide purity was assessed by high pressure liquid chromatography and peptide sequence was confirmed by amino acid analysis. Peptides were coupled to keyhole limpet hemocyanin (KLH) at a ratio of 50 peptides per KLH molecule (45). Mice and rabbits were immunized with the V γ peptides or C γ peptides, respectively. Animals were injected at three week intervals and the antisera screened for binding reactivity on peptide-KLH and peptide-bovine serum albumin conjugates to ascertain the presence of peptide-specific antibodies.

Monoclonal antibodies against the γ chain were generated by standard procedures as described in (47, 50). BALB/c mice were immunized with the KLH-coupled peptide to the variable region γ chain peptide described above using the method of Erickson and Merrifield (44). After four immunizations at two week intervals, spleen cells were fused with P3-X63-Ag801 myeloma cells. Positive hybridoma clones were screened and identified by the enzyme immunoassay (EIA) described in (48).

Isolation of DNA sequences of the δ polypeptide using sequences from purified proteins DNA sequences of the TCR δ gene may be isolated and determined by strategies utilized to isolate the TCR β gene as described in (49, 50). Briefly, the amino acid sequence of the TCR δ gene may be determined following isolation of the TCR δ polypeptide which is described hereinafter. After the amino acid sequence is determined, short, synthetic DNA sequences may be prepared using a commercial DNA synthesizer (Applied Biosystems, Inc., Foster City, Calif.). The synthetic DNA sequences may be used as probes for the isolation of the complete sequence of DNA from a cDNA library of cell lines containing the TCR δ polypeptide. The complete primary structure of the protein may then be determined (51).

Preparation of monoclonal antibodies against the δ polypeptides and against γ, δ complexes Monoclonal antibodies against the δ polypeptide may be generated by standard procedures (47, 50). Peptides derived ftom the TCR δ polypeptide may be prepared from nucleic acid sequences determined by the methods described above. Methods for selection of such peptides useful for immunization have been described in detail (55, 56, 57).

Monoclonal antibodies directed against γ, δ complexes may be prepared according to published procedures (47, 50). γ, δ complexes may be isolated from the T cell lines described above - and used to immunize BALB/c mice as described in previously published procedures (28). Alternatively, BALB/c mice may be immunized with cell lines, e.g., the IDP1 cell line or the IDP2 cell line.

Methods for the fusion, generation and maintenance of hybridoma cell lines have been widely published and are known to those skilled in the art. Hybridoma cells that produce monoclonal antibodies which are directed against specific TCR γ, δ cell lines but which do not cross react with other T cell lines may be selected and recovered.

Immunoprecipitations of TCR γ, δ and T3 from a human tumour and peripheral blood lymphocyte lines Viable lymphocytes were isolated by Ficoll-Hypague density gradient centrifugation and $2 \times 10^7$ cells were radio-iodinated by the lactoperoxidase technique as described (28). Labelled cells were lysed in 5 ml of TBS (10 mM Tris pH 8, 140 mM NaCl) with 0.3% 3-[(3-cholamidopropyl)dimethylammonio]-1-propanesulphonate (CHAPS), which preserves the TCR-T3 association (64), containing 2 mM phenyl methylsulphonyl fluoride (PMSF) and 8 mM iodoacetamide (IAA). Immunoprecipitation was carried out using fixed *Staphylococcus aureus* Cowan I (SACI) as described (12), and the immune complexes were washed $\times 5$ in TBS containing 0.1% Triton X-100 (TX-100). Reduced samples were boiled in 2 mM dithiothreitol (DTT) and all samples incubated for 10 rain at 23° C. in 10 mM IAA before analysis by SDS-PAGE. Immunoprecipitations using anti-C γ sera were performed on 1% TX-100 lysates that were dialysed to remove IAA and then denatured by the addition of one tenth volume of sodium dodecyl sulphate (SDS) containing 3 mM DTT with boiling for 3 min. After partial renaturation by the addition of 4 vols of 1.5% TX-100 in TBS containing 30 mM IAA, anti-C γ sera or NRS were added and the immunoprecipitates were washed in TBS containing 0.5% TX-100, 0.5% deoxycholate, 0.05% SDS before analysis by SDS-PAGE. Rat anti-mouse α chain-specific mAb 187.1 15 μg) was added as a second antibody to provide protein A binding of IgG$_f$ mAb $^\beta$F1, UCHT and P3 (53).

Northern blot analysis of RNA solated from PBL C1

Approximately 1.5 μg RNA was loaded per lane, probes were labelled to similar specific activity, and identical autoradiographical exposures are presented. RNA sizes were determined based on previously published lengths for TCR β and TCR γ transcripts (36, 4).

Two-dimensional gel analysis of TCR γ polypeptides and precursors

After radioiodination with lactoperoxidase, lymphocytes were treated with 100 U of neuraminidase (Gibco) in phosphate-buffered saline (PBS) 1 mg ml⁻ bovine serum ablumin, 1 mg ml$^{-1}$ glucose for 90 minutes at 23° C., washed in PBS and solubilized in 0.3% CHAPS. Immunoprecipitates were prepared as in FIG. 1 and NEPHGE (charge separation) was carried out using pH 3.5-10 ampholines (LKB, Sweden), or IEF using pH 3.5-10, 4-6, 9-11 amphollines (2:15.5:1.5) followed by 10.5% SDS-PAGE gels for size separation as described (12). NEPHGE was carried out (A, B) applying the iodinated IEF sample at the acidic end, while IEF (C,D) was carried out for 20 hours at 400 V applying the sample at the other (basic) end. Brackets enclsoe the T3-associated species.

Cells (2×10⁷) were preincubated for 1 hour at 37° C. in 4 ml methionine-free RPMI 1640 supplemented with 10% fetal bovine serum. $^{35}$S-methionine was added to 250 μCi ml$^{-1}$ and incubation was continued for 1 hour at 37° C. Cells were collected, washed and lysed 0.4 ml of boiling solution of 1% SDS, 10 mM Tris-HCl (pH 8.0), 0.1 mM PMSF and 10 mM IAA. Lysates were diluted with 1.6 ml of 2.5% Nonidet-P40, 1% gelatin, 10 mM Tris-HCl (pH 8) and 0.2 ml of 1 mg ml$^{-1}$ DNase. 0.5 mg ml$^{-1}$ RNase, 0.5M Tris-HCl (pH 7), 50 mM MgCl$_2$ and incubated at 0° C. for 2-4 hours. After centrifugation for 15 minutes at 12,000×g to pellet insoluble debris, immunoprecpitations with anti-γ serum were performed using protein A sepharose preincubated with 1% gelatin and washing as described (65). Elution from the immunoabsorbent and treatment with endo-H (Miles Scientific, Naperville, Ill.) were as described (65). Samples were analysed with anti-serum by two-dimensional gel electrophoresis employing NEPBGE in the first dimension and 10% SDS-PAGE in the second dimension, followed by fluorography (66).

Rearrangments of the γ and β genes in T cells expressing the TCR γ polypeptides

Genomic DNA was isolated as described (BamHI or EcoRI), size-fractionated on 0.7 & agarose (BamHI digests) or 0.9% agarose (EcoRI digest), and transerred to nitrocellulose as described (67). Filters were hybridized to a nick-translated $^{32}$P-labelled 0.8 kb HindIII-EcoRI J$_{γ1,3}$ probe (20) or a 1.1 kb EcoRI-HindIII C$_{β2}$ probe (68). Filters were washed in 2×SSC and 0.1% SDS tollowed by 0.2% SSC and 0.1% SDS at 55° C. before autoradiography with intensifying screens.

Cytolysis by IDP2 and PBL Cl cells

Cytolytic assays were performed in round-bottom 96-well tissue culture plates with $^{51}$Cr-labelling, harvesting and calculation of % specific release as described (34). IDP2 or PBL Cl cells were either preincubated with UCHT1 (1:300 dilution) (+anti-T3) for 30 minutes at 0° C., washed×3 or mock incubated and placed together with labelled target cells. Anti-HLA Class I and Class II mAb anti-T3 mAb were placed in wells containing the $^{51}$Cr-labelled MOLT 4 cells for 30 minutes at 0° C., then IDP2 cells were added at a 40:1 E:T ratio. All samples were assayed in triplicate, each experiment was performed at least three times, and one representative experiment of each is shown in FIG. 9.

Experimental Results

Figure 1B:
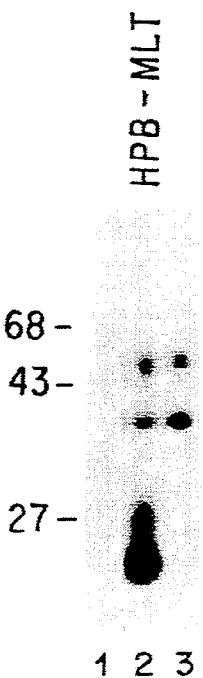
Figure 1C:
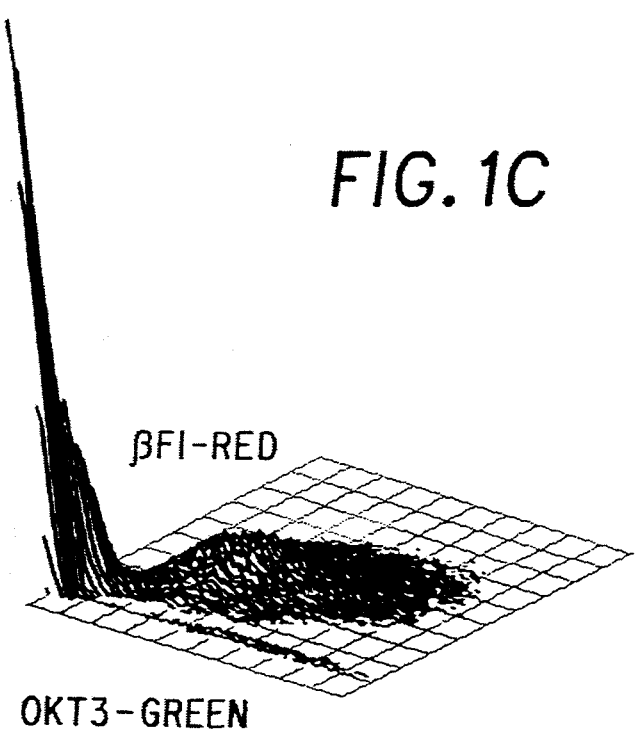

A murine framework antisere that recognizes the majority of human TCR α, β molecules has previously been reported (28). Subsequently, a murine monoclonal antibody, designated Framework 1 (βF1), that is reactive with shared determinants on the human TCR β chain was obtained (46). The βF1 monoclonal antibody reacts with the majority of T3 positive (T3+) human peripheral blood lymphocytes (PBLs) and is capable of inununoprecipitating the TCR α, β heterodimer from all human T cell lines examined that have α, βT cell receptors and express the T3 glycoprotein. Immunoprecipitations from a panel of T cell lines using this monoclonal antibody demonstrate this reactivity as well as the heterogeneity of the TCR u and TCR s subunits from different receptors (FIG. 1A). Like the framework antiserum (28), this monoclonal antibody does not stain the surface of living T cells, but will specifically react with both membrane and cytoplasmic T cell receptors after partial solution of the lymphocyte plasma membrane with 70% ethanol. Double staining of human PBLs with a fluorescein-anti-T3 monoclonal antibody and a biotinyl-βF1 monoclonal antibody followed by PE avidin reveals that the βF1 monoclonal antibody recognizes 95-97% of peripheral blood T3+lymphocytes. However, it clearly defines a small population of T lymphocytes that is βF1 negative (βF1−), yet T3+(FIG. 1C).

A second framework monoclonal antibody designated WT31, initially thought to recognize the T3 antigen (29), has recently been shown to react with a common epitope of human TCR α, β (30). While double staining with an anti-T3 monoclonal antibody (OKT-3) and WT31 revealed that each of these monoclonal antibodies cross-block binding of the other, one-color fluorescence indicated that WT31 typically recognized 1-3% fewer cells in peripheral blood than do anti-T3 monoclonal antibodies. The WT31 monoclonal antibody efficiently binds to the surface of T cells (such as in FACS analyses) and is capable of immunoprecipitating the TCR α, β molecules, albeit inefficiently, from radiolabeled detergent lysates (30) (FIG. 1B, lane 3). Thus, the βF1 monoclonal antibody and the WT31 monoclonal antibody appear to recognize all but a small fraction of human peripheral blood T3+cells, and define a subpopulation that is T3+but unreactive with both of these framework monoclonal antibodies against the TCR α, β molecules. Evidence that the T3 +lymphocytes that are unreactive with the monoclonal antibody βF1 are also unreactive with the monoclonal antibody WT31 is shown below. WT31 was used primarily for FACS analyses and βF1 was used primarily for immunoprecipitation studies.

Efforts at growing the WT31−T3+population from normal adult PBLs proved difficult, since the WT31−T3+lymphocytes usually overgrew the WT31−T3+cells following mitogenic stimulation. However, growth of the WT31−T3+population from the PBLs of immunodeficiency patients was successful. Immunodeficiency patient 1 (IDP1) suffered from the bare lymphocyte syndrome and lacked class II MHC antigen expression on lymphoid cells (31, 32), while immunodeficiency patient 2 (IDP2) suffered from an ectodermal dysplasia syndrome (33) and displayed poor in vitro T cell proliferative responses to mitogens.

After activation of PBLs from IDP1 with alloantigen and propagation in conditioned media containing interleukin-2 (IL-2) activity (34),the resultant cell line was observed to be approximately 50% WT31−T3+and 50% WT31−T3+(see Table I below, cell line 1). Subsequent sorting of this cell line yielded homogeneous populations of WT31−T3+cells and WT31−T3+cells (see Table I below, cell lines 2 and 3, respectively).

TABLE 1

| CELL LINE NUMBER | CELL LINE[1] SOURCE | DESCRIPTION | % POSITIVE WT31 | T3 | T4 | T8 |
|---|---|---|---|---|---|---|
| 1 | IDP1 | allo | 50 | 100 | 11 | 50 |
| 2 | IDP1 | WT31+ sort | 100 | 100 | 70 | 28 |
| 3 | IDP1 | WT31− sort | 0 | 100 | 0 | 62 |
| 4 | IDP2 | fresh PBL | 61 | 63 | 38 | 16 |
| 5 | IDP2 | PHA | 100 | 96 | 18 | 80 |
| 6 | IDP2 | allo | 2 | 100 | 0 | 43 |
| 7 | IDP2 | PHA | 12 | 93 | 1 | 18 |

Cell lines were also obtained from IDP2. Fresh PBLs from IDP2 revealed that 63% of the PBLs were T3+and 1−3% fewer cells (61%) were WT31+which is typical of normal PBLs (Table I, cell line 4). Activation of these IDP2 PBLs with either phytohemagglutinin (PHA) or alloantigen and propagation in vitro with conditioned media resulted in several cell lines. These included a homogeneous WT31−T3+cell line (Table I, cell line 5), a homogeneous WT31−T3+cell line (Table I, cell line 6) and on a third occasion, a cell line that was 88% WT31−T3+(with 12% contaminating WT31−T3+cells) (Table I, cell line 7). The WT31−T3+population contained both T4−T8+and T4−T8− cells (Table I, cell lines 3, 6 and 7). Further phenotypic analysis revealed that this population was T11+but negative for natural killer cell markers such as Leu 7, Leu 11 and OKM1 and for the immature thymocyte marker T6.

Figures 2A, 2B, 2C:
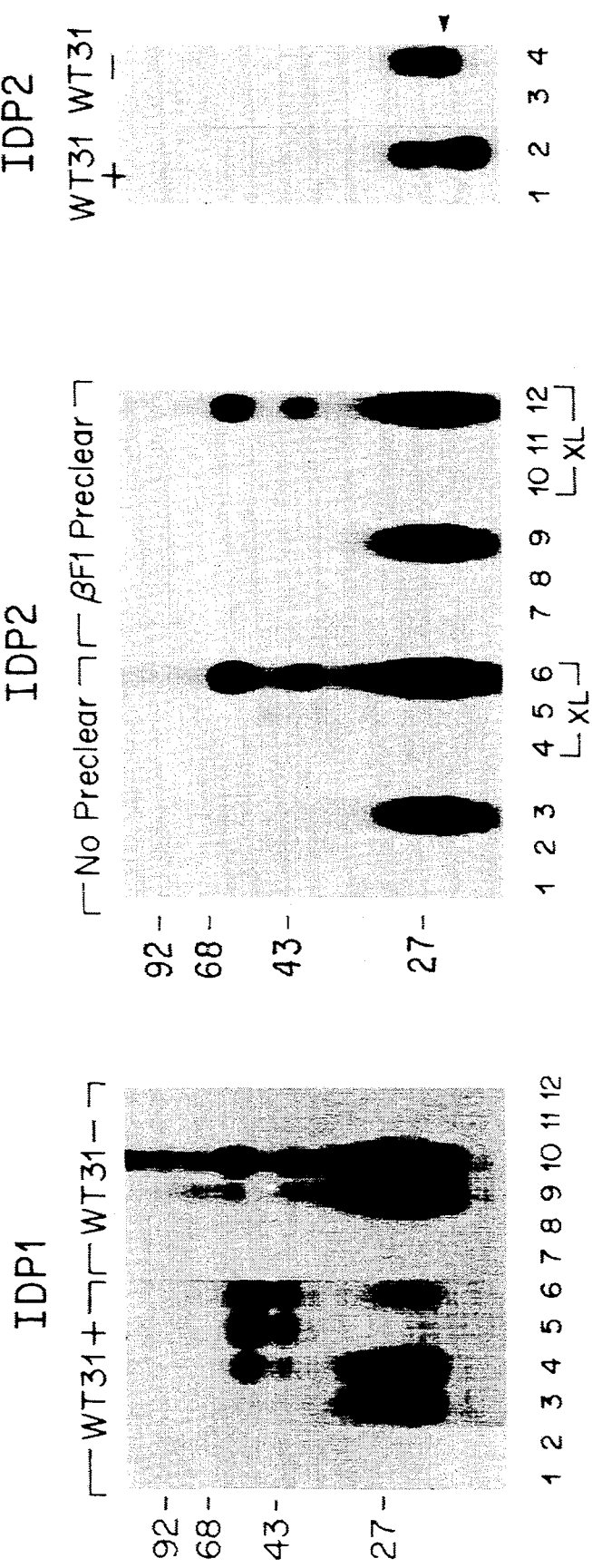

The βF1 monoclonal antibody immunochemically defined a heterodimeric structure on the surface of $^{125}$I-labeled WT31−T3+IDP1 lymphocytes (FIG. 2A, lane 5), yet failed to recognize a similar protein on the WT31−T3+population from this same individual (FIG. 2A, lane 11). Similar analysis of IDP2 cell lines revealed a trace of TCR α, β on the 88% WT3−T3+cell line 7 (FIG. 2B, lane 2) consistent with the 12% contamination with the WT31−T3+cells. Thus, the WT31−T3+cells, identified by the lack of cell surface reactivity with the WT31 monoclonal antibody in FACS analysis, were also βF1−, as determined by the lack of TCR α, β on immuno-precipitation. All WT31−T3+and WT31−T3+cell lines expressed similar amounts of T3 by FACS analysis and by immuno-precipitation with an anti-T3 monoclonal antibody (FIG. 2A, lanes 3 and 9; FIG. 2C, lanes 2 and 4). However, the T3 molecule found on WT31−βF1−T3+ lymphocytes was not identical to the T3 molecule found on WT31−βF1+T3+cells by SDS-PAGE. One-dimensional (FIG. 2C) and two-dimensional gel analysis indicated that the difference in T3 was restricted to the light T3 subunits, which reproducibly displayed different SDS-PAGE mobilities (FIG. 2C, arrowhead).

Figures 3A, 3B:
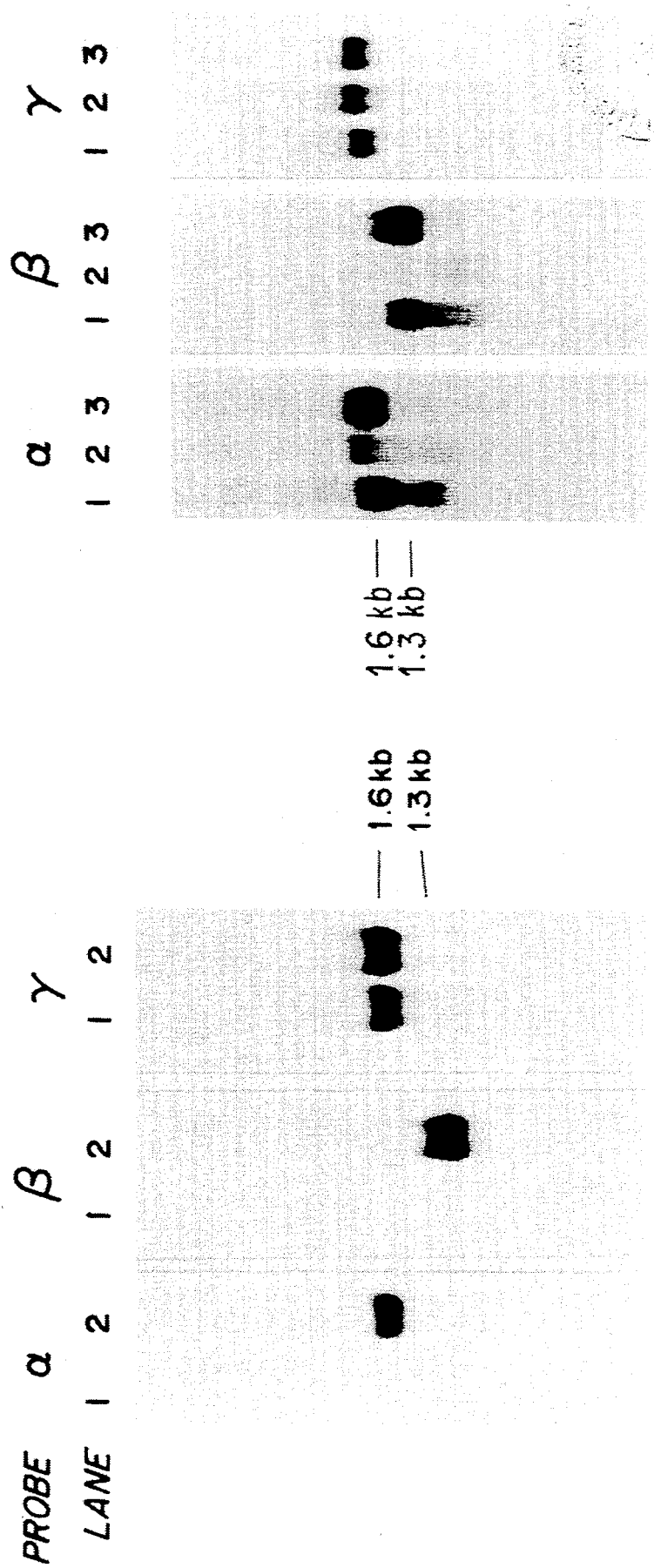

To determine if the WT31−βF1−T3+population lacked TCR α, β molecules, or alternatively expressed TCR α, β molecules that failed to react with these monoclonal antibodies, the presence of mRNAs encoding the TCR α and β proteins was investigated. $^{32}$P-labeled cDNA clones encoding TCR α, β TCR γ and TCR were used to probe Northern blots containing whole cell RNA from WT31−βF1−T3+ and WT31+βF1+T3+ IDP2 cell lines and from HPB-MLT, which is known to contain mRNA for TCR α, TCR β and TCR γ. No TCR$^α$ or TCR$^β$ mRNA transcripts could be detected in the RNA from the WT31−βF1−T3+IDP2 cell line δ (FIG. 3A- probe, lane 1; or β-probe, lane 1), whereas expression of both was clearly detectable in RNA from HPB-MLT (FIG. 3A α-probe, lane 2; and β-probe, lane 2). Notably, TCR γ mRNA was present in the WT31−T3+cells at levels comparable to that in HPB-MLT (FIG. 3A γ-probe, lanes 1 and 2). Thus, the WT31−βF1−T3+ lymphocytes lacked TCR and mRNA. Subsequent experiments on cell lines that were mostly WT31−T3+corroborated these results. For example, Northern blot analysis performed on IDP2 cell line 7 (88% WT31−T3+) and compared with IDP2 cell line 5 (WT31−T3+), as well as with HPB-MLT cells, revealed only a trace of TCR or TCR β mRNA in the 88% WT31−T3+cells (consistent with the 12% contamination with WT31−T3+cells) (FIG. 3B, lane 2 for each probe). Further, the majority of the β transcripts that could be detected were 1.0 and not 1.3 kb and were probably nonfunctional (35). In contrast, the IDP2 cell line 5 (WT31−T3+) expressed levels of both RNA species which were comparable to HPB-MLT (FIG. 3B, lane 1 for each probe). However, like the WT31−T3+cell line shown in FIG. 3A, both the WT31−T3+and the WT31−T3+cell lines showed TCR γ RNA levels comparable to HPB-MLT (FIG. 3B γ-probe). Thus, the WT31−T3+cells lacked and 8 T cell receptor mRNA (Northern analysis) and α and β T cell receptor proteins. (immunoprecipitation and FACS analysis). The presence of TCR γ mRNA in WT31−T3+cells, while Consistent TCR γ protein expression, could not be taken as strong evidence for this, since many human cell lines that express TCR γ mRNA of normal size may express full length transcripts that are out of frame due to defective V-J joining (36).

To determine if proteins analogous to the TCR α, β molecules existed on the WT31−βF1−T3+cells, the technique of chemical cross-linking was utilized. This procedure has been used to shown directly the physical association of the TCR α, β molecules with the T3 glycoprotein (12). The bifunctional, cleavable reagent, dithio-bis-succinimidyl propionate (DSP) was employed to cross-link $^{125}$I-labeled surface proteins of viable T lymphocytes. After cross-linking, the lymphocytes were solubilized in a non-ionic detergent and immunoprecipitated with an anti-T3 monoclonal antibody. As expected, the WT31−βF1+T3+lymphocytes revealed that the TCR α and β and chains were cross-linked to T3. For example, TCR α, β molecules and T3 were found in anti-T3 or βF1 monoclonal antibody immunoprecipitates from cross-linked IDP1 cell line 2 (WT31+T3+) (FIG. 2A, lanes 4 and 6). However, despite the lack of reactivity with the βF1 monoclonal antibody and lack of TCR α or TCR β mRNA, IDP1 cell line 3 (WT31−T3+) and IDP2 cell line 7 (88% WT31−T3+) both expressed two protein subunits ($M_r$ 55,000 and 40,000) that specifically cross-linked to T3 ( FIG. 2A, lane 10; FIG. 2B, lane 6). The mobilities of these T3 associated molecules were clearly different from those of the TCR α and β chains from WT31−T3+cell lines (compare FIG. 2A, lanes 4 and 10; or FIG. 2B, lanes 5 and 6).

Since IDP2 cell 1 lne 7 (88% WT31−T3+) contained 12% WT31−T3+cells, accounting for the weak βF1 immunoprecipitates noted (FIG. 2B, lane 2), the lysate from these cells was precleared of TCR α, β protein using the βF1 monoclonal antibody. After preclearing, no anti-T3 monoclonal antibody, $M_r$ 55,000 and 40,000 residual βF1 reactive material could be detected (FIG. 2B, lanes 8 and 11). When this βF1- precleared lysate from cross-linked cells was immunoprecipitated with an anti-T3 monoclonal antibody, $M_r$ 55,000 and 40,000 subunits were still detected (FIG. 2B, lane 12).

Since these WT31−βF1−T3+cell lines display undetectable levels of TCR α and TCR β mRNA, the molecules found specifically cross-linked to T3 on their cell surfaces cannot represent proteins encoded by the known TCR or TCRβ genes.

cDNA clones representing the rearranging human TCR γ gene would encode a polypeptide with a predicted molecular weight of 40,000 daltons (36). However, unlike the murine TCR γ gene, which does not reveal any N-linked glycoslyation sites (15), the human TCR γ gene reveals five potential sites for N-linked glycosylation, four of which are located in the constant region (36). Since a TCR γ protein has not previously been isolated, it is not known how many of these potential sites may be used. However, a fully glycosylated human TCR γ protein may have a $M_r$ of about 55,000. The heavy chain of the non-α-non-βT3-associated subunits identified on the WT31−βF1−T3+IDP1 and IDP2 cell lines has a relative mobility on SDS-PAGE of 55,000 daltons (FIG. 2A and 2B).

In order to determine if this T3-associated heavy chain was serologically cross-reactive with or identical to the TCR γ protein, antisera were raised to a synthetic peptide having the sequence:

*RTKSVTRQTGSSAEITC*

(representing a 17 amino acid stretch of residues 5-21 from the variable region; anti-V γ peptide serum) and to a synthetic peptide having the sequence:

*DKQLDADVSPKPTIFLPSIA*

Figure 4A:
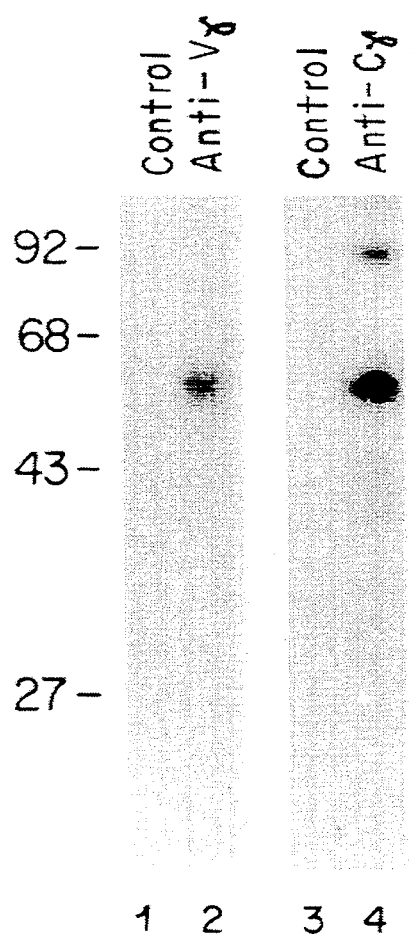

(representing a 20 amino acid stretch of residues 117-136 from the constant region; anti-C γ peptide serum) of the TCR γ amino acid sequence deduced from a human cDNA clone (36). Both the anti-C γ peptide serum and anti-V γ peptide serum immunoprecipitated a molecule with $M_r$ 55,000 from the denatured lysate of $^{125}$I-labeled WT31−βF1−T3+cells (FIG. 4A, lanes 2 and 4). Such molecules could not be immunoprecipitated from lysates of $^{125}$I-labeled HPB-MLT cells, which express only nonfunctional TCR γ mRNA (36)

Figure 4B:
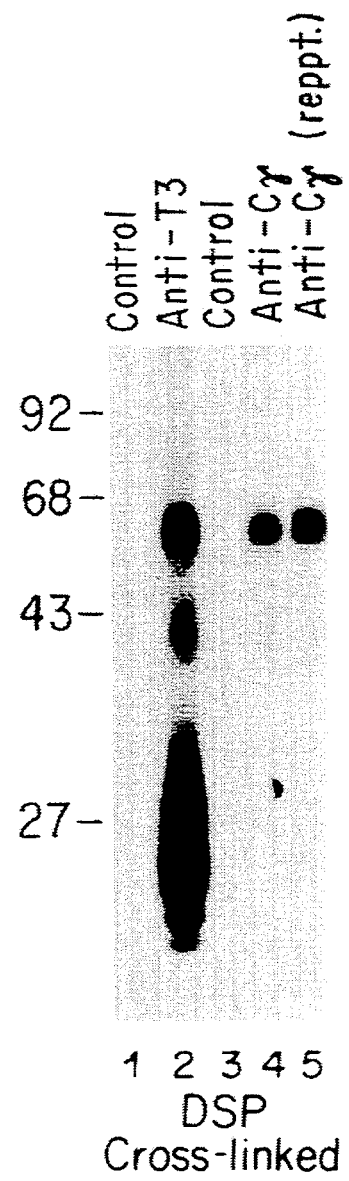

To demonstrate that the 55,000 dalton molecule immunoprecipitated by the anti-C γ and anti-V γ peptide sera was, in fact, the heavy chain subunit that cross-linked to T3 , an additional experiment was performed (FIG. 4B). A sample of DSP cross-linked lysate from the WT31−βF1−T3+cells was first immunoprecipitated with an anti-T3 monoclonal antibody, again demonstrating the presence of $M_r$ 55,000 and 40,000 subunits associated with T3 (FIG. 4B, lane 2). In parallel, another aliquot of the cross-linked lysate was immunoprecipitated with an anti-T3 monoclonal antibody, and the immunoprecipitated T3 cross-linked polypeptides were eluted from the immunoabsorbent under denaturing and reducing conditions in order to break the DSP cross-link. This eluate was then re-precipitated with anti-C γ peptide serum. The $M_r$ 55,000 subunit that cross-linked to T3 was re-precipitated by anti-γpeptide serum (FIG. 4B, lane 5), indicating that the $M_r$ 55,000 subunits defined by these two approaches were identical.

Figure 5A:
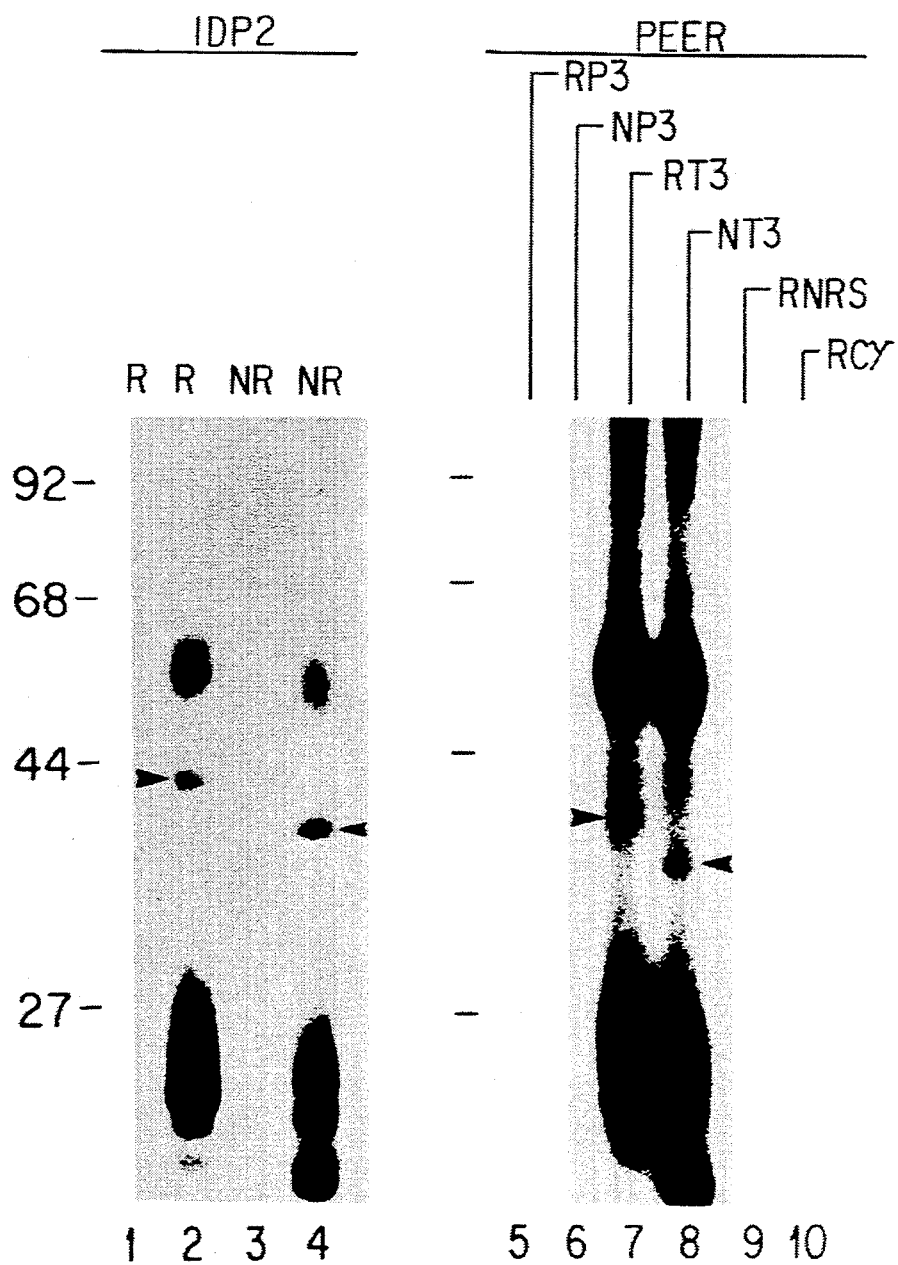

Immunoprecipitations from lysates of surface-iodinated IDP2 lymphocytes using anti-T3 mAb (under conditions that do not dissociate TCR subunits from T3, see FIG. 5) yielded two species (55K and 40K) in addition to the T3 subunits (FIG. 5A). This result is identical to the one reported previously using chemical cross-linking. The 55K species was shown to react specifically with anti-C γ and anti-V peptide sera. The 40K polypeptide was unreactive with these anti-Y peptide sera and is thus likely to represent a non TCR α, β or γ subunit, namely δ. To determine if these subunits are covalently linked, like the TCR α and β subunits, the T3 co-immunoprecipitated polypeptides were examined under reducing and nonreducing conditions. In striking contrast to the TCR α, β subunits, which exist in a heterodimeric disulphide-linked form under nonreducing conditions, the TCR γ and δ subunits on the IDP2 cell line are not covalently linked (FIG. 5A). A small increase in relative mobility on SDS-polyacrylamide gel electrophoresis (PAGE) under nonreducing conditions was observed for the diffuse, heavily glycosylated (see below) TCR γ, whereas a dramatic increase in moblility was observed for the δ subunit, suggesting the presence of one or more intrachain disulphide loops (compare species at arrows, lanes 2 and 4).

Weiss, et al. suggested that the PEER cell line might express the TCR γ polypeptide since it lacked expression of TCR mRNA yet expressed a T3-associated 55–60K polypeptide (69). On further examination, this cell line was found to lack reactivity with a mAb recognizing framework determinants on the TCR β chain, βF1 (FIG. 5A) and to express a strongly iodinated 38K polypeptide. The 55–60K polypeptide was specifically immunoprecipitated with anti-C γ peptide sera and thus appears to represent a further example of the TCR γ protein (FIG. 5A). The TCR γ and δ polypeptides on PEER were of similar size to those on the IDP2 cell line and similarly were not disulphide-linked. Like the δ subunit on IDP2 cells, the counterpart molecule on PEER underwent a marked shift in SDS-PAGE mobility when compared under reducing and nonreducing conditions (compare species at arrows, lane 7 and 8). Thus the IDP2 and the PEER cell lines appear to express similar types of TCR γ, δ−T3 complexes, in which the TCR γ and δ subunits are not covalently linked.

Figure 5B:
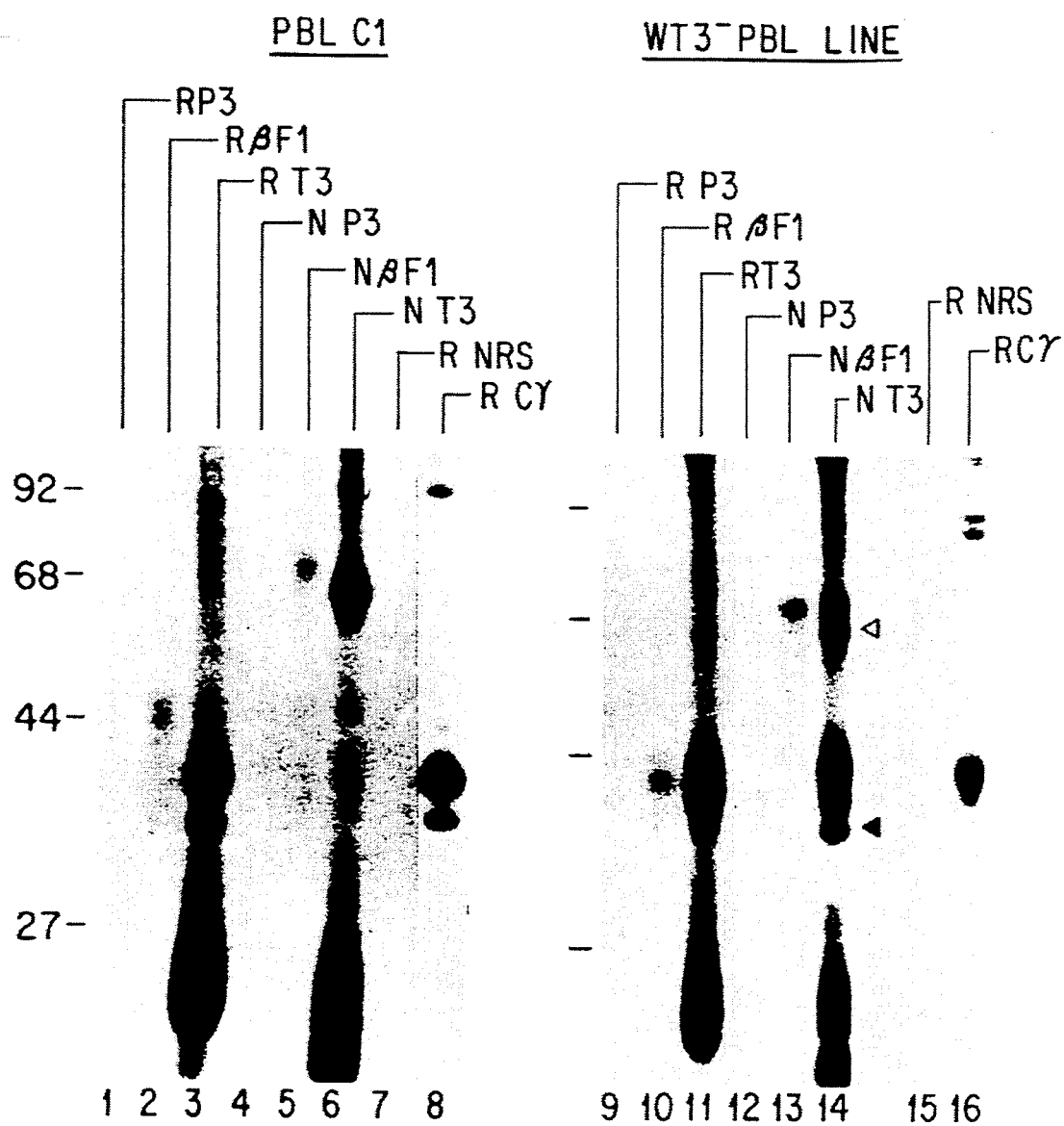

We wished to determine if this second TCR was also expressed as a component of the T cell population in normal peripheral blood. Two-colour cytofluorographic analysis comparing staining of human peripheral blood lymphocytes (PBL) with mAb βF1 and OKT-3 showed a discrete population representing 2-5% of the T3+PBL that appeared to be TCR α, β negative. To examine this lymphocyte population, normal adult PBL were subjected to cytofluorographic cell sorting after staining with mAb WT31. Unstained PBL were isolated and propagated in vitro in IL-2-containing conditioned media receiving biweekly additions of irradiated autologous feeder cells and phytohaemagglutinin (PHA-P). The cell line derived, WT31−PBL−LINE was cloned by limiting dilution with plating at 0.5 cell well and the cloned cells were propagated as for the polyclonal cell line. Several such peripheral blood derived T cell clones were obtained, and PBL Clone 1 ( PBL C1) was studied in detail. By cytofluorographic analysis, this clone was T3+T11− but T4−T8− and WT31−. The expression of TCR α, β and γ mRNA from PBL C1 was determined by Northern blot analysis (FIG. 6). By comparison with the WT31+βF1+T cell tumor HPB-MLT, only very low levels of TCR and s mRNA were detected. In contrast, abundant TCR γ mRNA was noted (FIG. 6 probe); interestingly, the TCR γ mRNA was slightly smaller than the 1.6 kilobase (kb) message found in HPB-MLT and in the TCR γ-expressing IDP2 cell line (FIG. 6). Consistent with these observations, WT31 reactivity was not detected in cytotluorographic analysis (data not shown) and only scant levels of TCR α and β polypeptides were found by immunoprecipitation using mAb βF1 (FIG. 5B, lanes 2, 5). In contrast it is likely that the trace levels of TCR α and β protein detected in PBL C1 are accounted for by the 1–2% contamination wxth irradiated autologous feeder cells used in the propagation of this clone. Two abundant chains (40K and 36K) were observed associated with T3 under reducing conditions in SDS-PAGE analysis (FIG. 5B, lane 3). Anti-C γ sera immunoprecipitated both of these polypeptides trom reduced and denatured PBL C1 lysates (FIG. 5B, lane 8).

To determine if these 40K and 36K TCR γ polypeptides were part of a disulphide-linked dimer, coimmunoprecipitations with anti-T3 were examined under nonreducing conditions. A single ban ot $M_r$ (70K) was observed indicating that, unlike IDP2 and PEER cells, PBL C1 expresses a T3-associated TCR γ gene product that is part of a disulphide-linked dimeric complex.

Figure 7A:
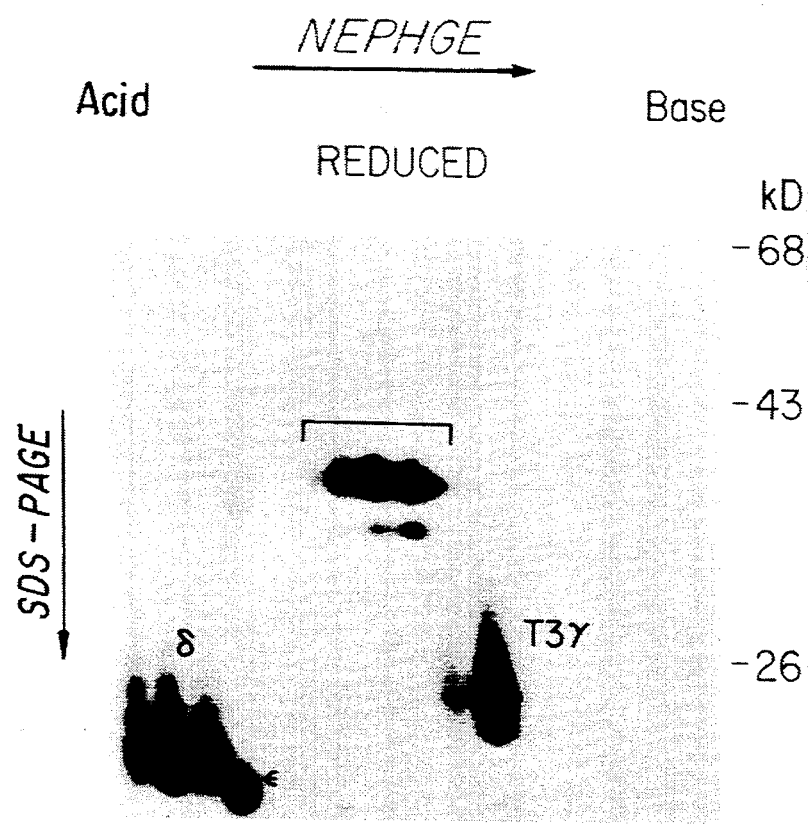

As a TCR γ partner (δ) was present on the non-disulphide linked form of this receptor complex on IDP2 and PEER cells, we examined whether the disulphide-linked form of the receptor on PBL C1 was composed of a homo- or a heterodimer. Immunoprecipitates were analysed by two-dimensional gel electrophoresis (nonequilibrium pH gel electrophoresis (NEPHGE) followed by SDS-PAGE; FIG. 7A, B). Under reducing conditions, both the TCR γ species (40K and 36K) were found to have identical charges, and displayed heterogeneity typical for a sialylated glycoprotein. These characteristics are like those described previously for differentially glycosylated TCR u polypeptides having the same amino-acid backbone. Thus, these species may represent differentially glycosylated forms of the same TCR γ peptide. This conclusion is supported by the results of metabolic pulse-labelling (below) which reveal only a single precursor TCR γ species in PBL C1.

Figure 7B:
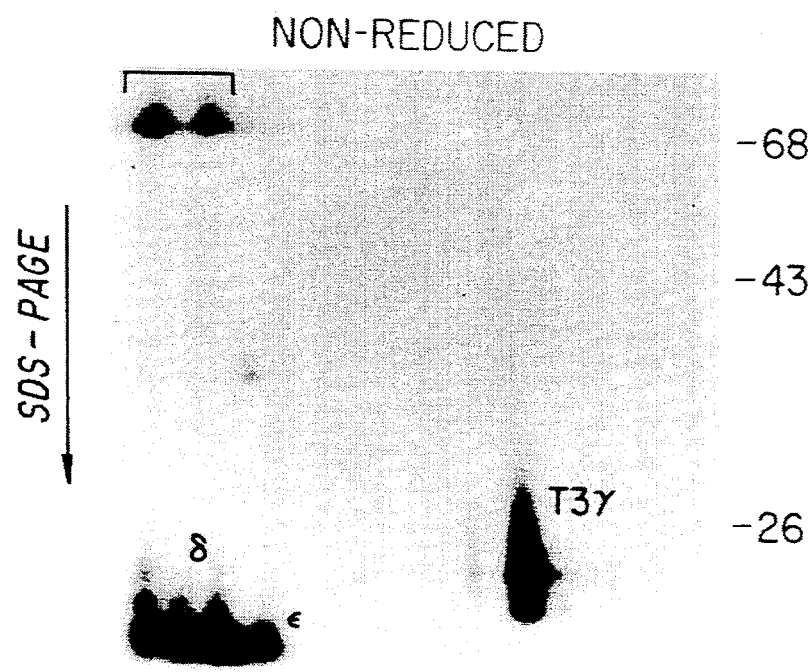
Figure 7C:
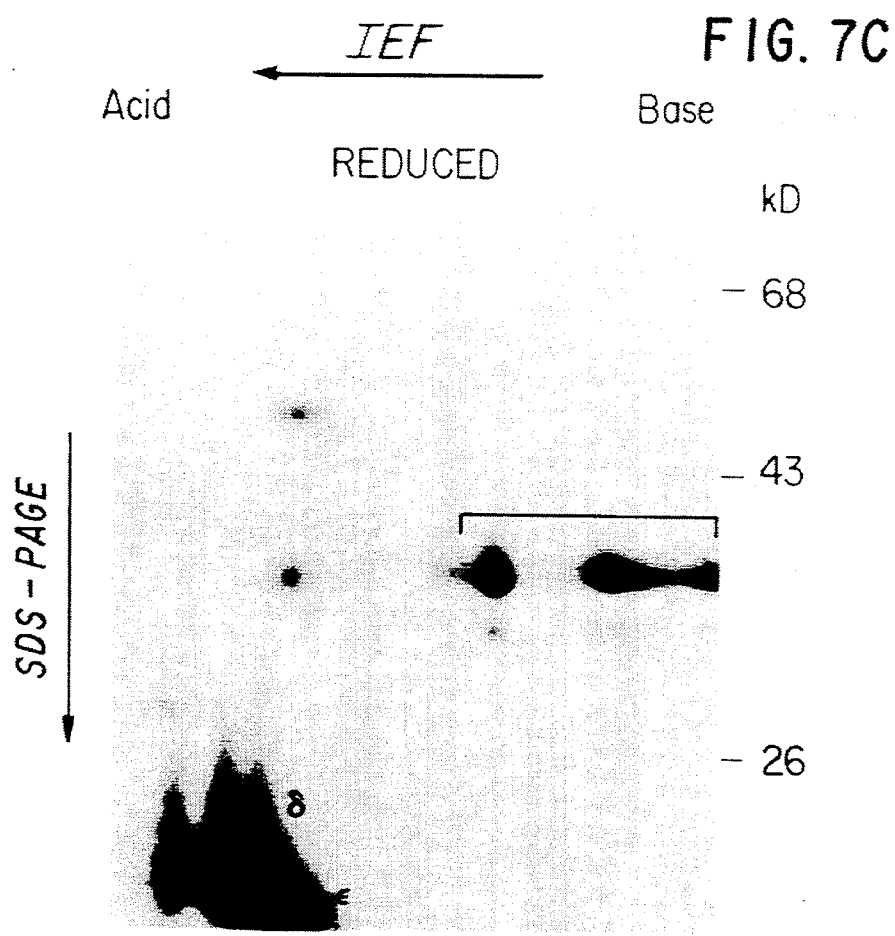
Figure 7D:
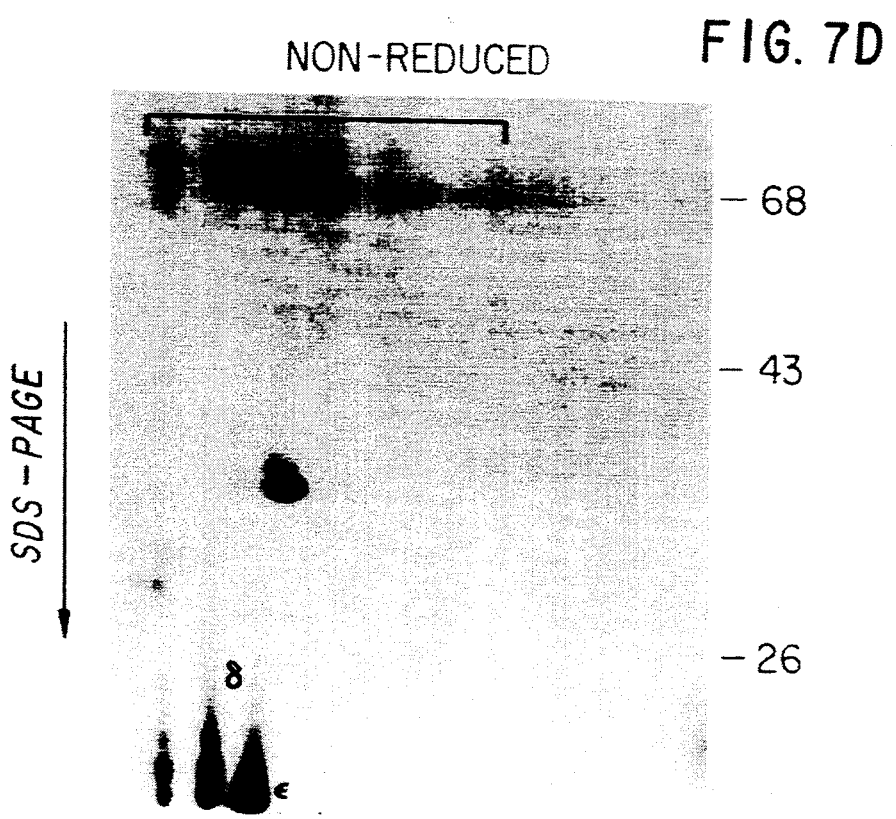

A disulphide-linked dimer composed of one or both of these TCR γ species should have a focusing position similar to either of the two components alone when analysed by NEPHGE or equilibrium isoelectric focusing (IEF). But a heterodimer composed of TCR γ and a distinct polypeptide might have a different charge and focusing position. The position of the disulphide-linked dimer was therefore examined by carrying out NEPHGE under nonreducing conditions, followed by SDS-PAGE under nonreducing conditions (FIG. 7B). Strikingly, the position of the disulphide-linked dimer was substantially more acidic than that of the TCR γ polypeptides examined under reducing conditions (compare the 40K and 36K species in FIG. 7A with the 70K species in FIG. 7B). This result suggests that the TCR γ species were covalently linked to a polypeptide of distinct NEPHGE mobility. Thus, although a TCR γ partner could not be directly visualized (either because it was inadequately labelled with $^{125}$I or because it did not resolve in the focusing system used here), the TCR γ polypeptide on PBL C1 appeared to be expressed as a part of a disulphide-linked heterodimer. Experiments using equilibrium IEF (rather than NEPHGE) confirmed this observation (FIG. 3D).

Figure 7E:
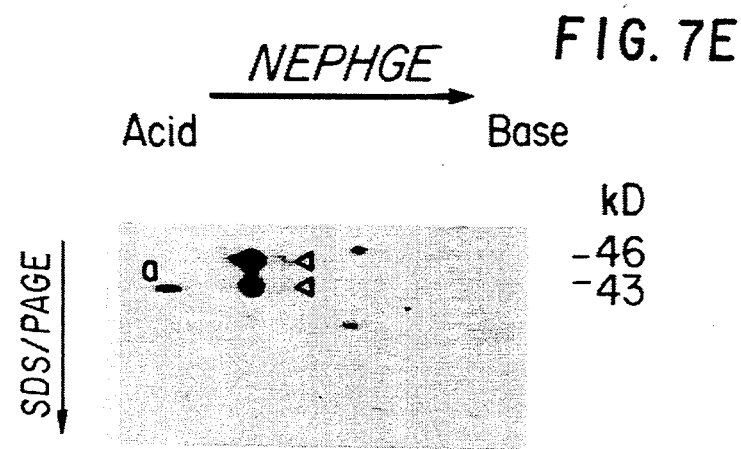
Figure 7F:
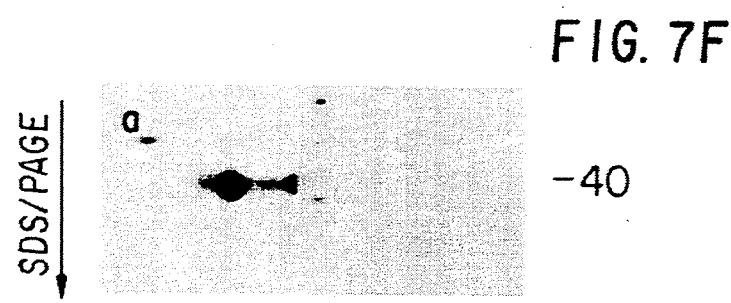
Figure 7G:
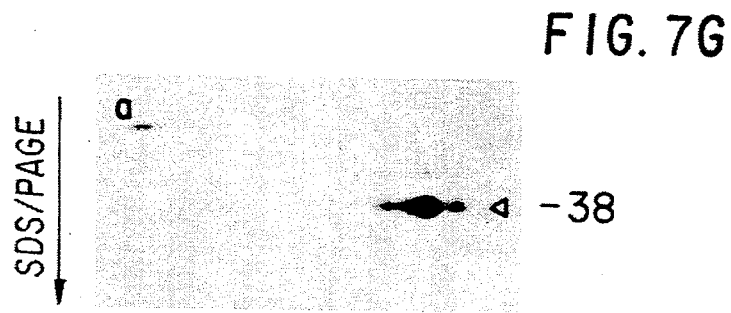
Figure 7H:
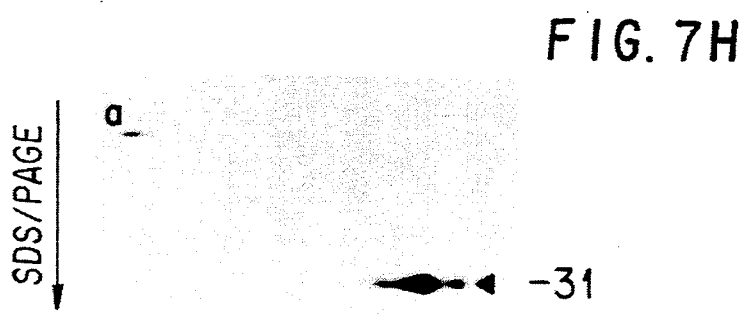

A further distinction between the disulphide-lxnked and non-linked forms was the size of the mature TCR γ glycopeptide (55–60K on IDP2 and PEER versus 40K and 36K on PBL C1). To assess how much of this radical size difference is due to difEerential glycosylation and how much to different peptide backbones, TCR γ peptides were analysed in cells pulse-labelled with $^{35}$S-methionine. After solubilization under denaturing and reducing conditions, the lysates were immunoprecipitated with anti-C γ sera and examined by two-dimensional gel electrophoresis (FIG. 7E–H). Immunoprecipitates were either treated with endoglycosidase H (endo-H) to remove immature high-mannose glycans from Pulse-labelled material, or were mock treated. Two TCR γ polypeptides (46K and 43K) of identical NEPHGE mobility were synthesized by the IDP2 cell line. Treatment with endo-H reduced both forms to a 40K form, suggesting that the 46K and 43K forms carried different numbers of carbohydrates, and that a single TCRγ polypeptide backbone (40K) was synthesized by IDP2 cells (FIG. 7E, F). In contrast, a more basic, 38K glycosylated form was synthesized by PBL C1 , which after endo-H digestion displayed a nonglycosylated 31K peptide backbone (FIG. 7G, H). Thus the TCR γ polypeptides on the non-disulphide-linked (IDP2) and the disulphide-linked (PBL C1) forms characterized here have radically different peptide backbone sizes (40K and 31K respectively). The fact that the glycosylated TCR γ peptides observed Dy pulse-labelling are of different molecular weight than those ound by cell surface iodination presumably results from the different types of carbohydrates they carry, namely high-mannose versus complex.

We next wished to determine if both a disulphide-linked and a noncovalently associated form occurred in normal adult peripheral blood. The polyclonal peripheral blood cell line (WT31−PBL LINE) from which PBL C1 had been cloned was therefore studied in greater detail. WT31−PBL LINE was homogeneously T3+Tll+and contained 95% WT31−T4−T8− with 5% contaminating WT31+cells. When examined by immunoprecipitation from iodinated, solubilized cells, weak but detectable reactivity with mAb βF1 was observed (FIG. 5B, lanes 10 reduced and 13 nonreduced), consistent with the expected 5% TCR α, β positive lymphocytes. In contrast, anti-T3 mAb immunoprecipitated large amounts of both T3 and associated polypeptides of 35–45K under reducing conditions (FIG. 5B, lane 11). To determine what fraction of these were disulphide-linked, the T3 immunoprecipitate was examined under nonreducing conditions (FIG. 5B, lane 14). Less than half of the T3-associated polypeptides were disulphide-linked. This material included disulphide-linked TCR α, β peptides located above the open arrow, lane 14 (size identified by the βF1 precipitate, lane 13) and disulphide-linked TCR γ peptides of smaller size (open arrow, lane 14). Strikingly, the majority of the T3-associated species were not disulphide-linked and migrated with the same mobility under both reducing and nonreducing conditions. Notably, a fraction of these non-linked species displayed a marked increase in SDS-PAGE mobility under nonreducing conditions, similar to the TCR δ on the IDP2 and PEER cells (see FIG. 5B, lane 14, solid arrow). Reactivity with anti-C γ sera confirmed that most of the labelled material associated with T3 expressed on WT31−PBL LINE was TCR γ gene products (lane 16).

Thus, the protein product of the TCR γ gene occurs on T3+lymphocytes in adult peripheral blood in both disulphide-linked and unlinked molecular forms. Moreover, the non disulphide-linked form of TCR γ may be further divided into 55–60K glycosylated (IDP2 and PEER) or 35–45K glycosylated (thymic T cell clone C11 (70) and WT31−PBL LINE) species.

TCR γ and e gene rearrangements were examined in T cells known to express the TCR γ polypeptide on their cell surfaces. Southern blot analysis were carried out using the 0.8 kb EcoRI-HindIII human $J_{\gamma1,3}$ probe (nomenclauture according to Quertermous et al. (71)). This probe detects germline bands of 23kb and 12kb in a BamHI digest of genomic DNA. The 23 kb band encompasses $C_{\gamma1}$ and the 12 kb band encodes $C_{\gamma2}$. Using this probe, IDP1, PBL C1 and PBL C2 (also derived from the WT31−PBL LINE) showed rearrangements of the TCR γ gene (both PBL C1 and PBL C2 displayed an identical rearrangement; FIG. 8A).

Seven rearrangements in PBL using the $J_{\gamma1,3}$ probe and EcoRI-digested genomic DNA in Southern blot analyses have been detected (20). Six (I, II, III, IV, VII and V) of these seven rearrangements are shown in PBL, fetal thymus, and newborn thymus genomic DNA (FIG. 8B; see arrows and rearrangement nmbers). Four rearrangements (I, II, VI and VII) either are not used by peripheral blood lymphocytes which express the TCR γ polypeptide or cells demonstrating them were lost under the propagation conditions used for the WT31−PBL LINE.

Nevertheless, the WT31−PBL LINE DNA revealed at least three of these rearrangements (III, IV and VI) (FIG. 8B, lane 3) and these same rearrangements were used by IDP2, PBL C1 and PBL C2 (data not shown for the EcoRI digest) and all of these rearrangements are displayed in fetal thymus.

The TCR β gene was al so rearranged in IDP2, PBL C1 and PBL C2 cells. The 1.1 kb EcoRI-HindIII $C_{\beta2}$ probe detects a germline band of 20 kb which encompasses both C β constant regions in a BamHI digest of genomic DNA (68). One predominant TCR β rearrangement for IDP2 and two identical rearrangements for PBL C1 and PBL C2 were observed (FIG. 8C). It is assumed that these TCR β rearrangements are nonproductive based on the immunoprecipitations and Northern analyses for these cell lines. As both PBL C1 and PBL C2 have the same TCR γ and β rearrangements, they appear to be clonal and derived from the same cell within the WT31−PBL LINE.

Figure 9C:
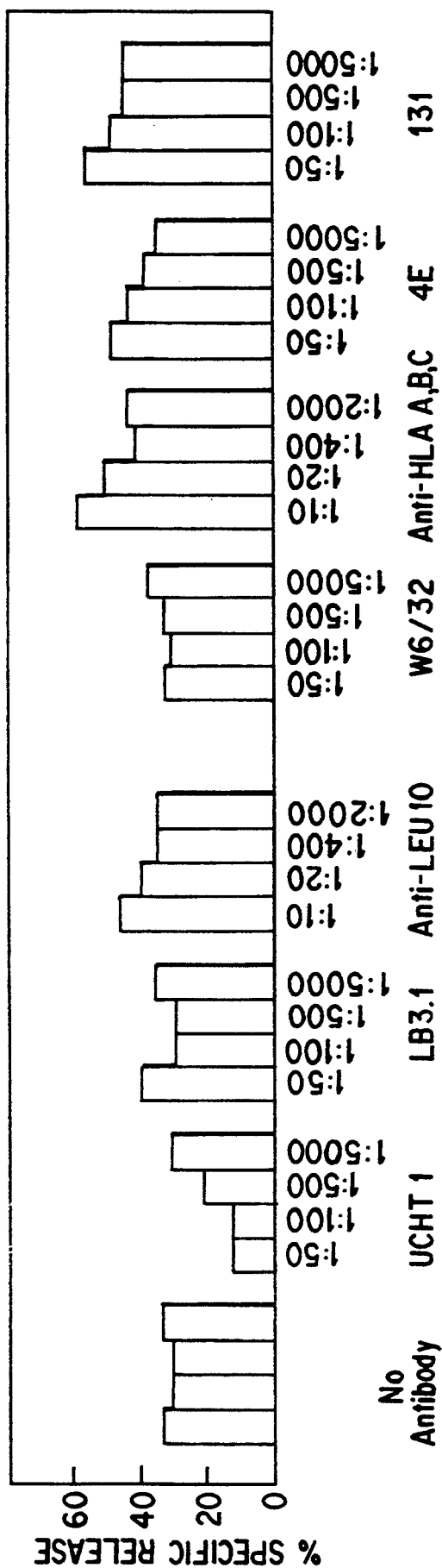

As TCR γ -expressing cells were found in adult peripheral blood, functional studies were carried out to determined whether they have effector capabilities. When IDP2 and PBL C1 were examined for their ability to lyse target cells in $^{51}Cr$ release assays, they proved to have spontaneous efector cytotoxic capability (FIG. 9). Although the IDP2 cell line did not lyse the majority of natural killer (NK) targets or PHA blasts ft allogeneic PBL, they were selectively capable of lysing $^{51}Cr$-labelled MOLT-4 cells (FIG. 9A top). In two of six similar assays, weak lysis (10–15% $^{51}Cr$ release) of K562 targets was also observed. Lysis of MOLT-4 cells was not inhibited by a variety of mAb directed against monomorphic MHC Class I (W6/32 anti-HLA-A, B, C, 4E and 131) or Class II (LB3.1 and anti-Leu 10) determinants (FIG. 9C), although we have previously found that these mAb efficiently block killing by both MHC Class I and Class II allospecific CTL (34). These data suggest that lysis of MOLT-4 cells was MHC class I and II independent. Only anti-T3 mAb partially blocked the specific lysis of MOLT-4 cells (FIG. 9C). On the other hand, when triggered by prebinding of anti-T3 mAb to IDP2, as has been previously reported for thymic-derived CII[7], $^{51}Cr$-labelled target cells that express Fc receptors for IgG (for example, U937), were efficiently lysed (FIG. 9B, +anti-T3). Such killing could be completely inhibited by aggregated human IgG, confirming that this T3-mediated lysis occurred through a mechanism of enhanced conjugate formation via IgG Fc receptors (data not shown). The paradoxical augmentation of lysis by anti-T3 mAb for some targets (U937) and the blocking of lysis for specifically recognized targets (MOLT-4) might result from the competing effects of triggering and increasing conjugate formation via T3 but sterically blocking antigen recognition via the TCR.

PBL C1 proved a more efficient killer cell than IDP2. PBL C1 displayed spontaneous cytolytic activity against K562 cells (MHC Class I and II negative) showing nearly 50% specific $^{51}Cr$ relsease when examined at an effector target (E:T) ratio of 20:1 (FIG. 9D top). Moreover, PBL C1 also lysed MOLT-4 cells and to a lesser extent, CEM cells. No lysis of Daudi, U937, or either autologous or allogeneic PBL was detected. Triggering with anti-T3 mAb induced PBL C1 to lyse the U937 cell line. Further, Iysis of K562 was slightly augmented while that of MOLT-4 was partially inhibited (FIG. 9E). Taken together, the spontaneous cytolytic activity of IDP2 and PBL C1 on turnour targets such as K562 and MOLT-4 and the failure to block such activity by anti-MHC mAb indicates that these TCR γ lymphocytes are non-MHC class I and class II restricted cytotoxic T lymphocytes.

DISCUSSION

Framework monclonal antibodies against the TCR α, β molecules, β F1 and WT31, were used to identify and isolate the WT31−βF1T3+lymphocyte population from the peripheral blood lymphocytes of two immunodeficiency patients. By the criteria of both immunoprecipitation analysis with t tamework monoclonal antibodies and Northern blot analysis using TCR and TCR β specific cDNA probes, polyclonal human T cell lines of this phenotype were shown to express neither TCR α, β mRNA transcripts nor polypeptides. Nevertheless, chemical cross-linking studies using the cleavable DSP reagent revealed the existence of a protein complex associated with the T3 glycoprotein on the surface of these cells. The heavier of the two subunits that cross-lxnked to T3 ($M_r$ 55,000) was also immunoprecipitated by two different antisera, one generated against a 17 amino acid synthetic peptide corresponding to a part of the variable region and another generated against a 20 amino acid synthetic peptide corresponding to a part of the constant region of the deduced amino acid sequence of a rearranged TCR γ gene (19, 36) Thus, the $M_r$ 55,000 protein is the TCR γ protein encoded by the rearranging TCR γ gene (15). The $M_r$ 40,000 polypeptide is a fourth T3-associated protein designated TCR δ (FIGS. 2A and 2B). The TCR γ and TCR δ polypeptides form a T3-associated heterodimeric structure on these cells (TCR γ, δ-T3) that is analogous to the previously described T cell receptor complex (TCR α, β).

The TCR γ lymphocytes examined here exhibit non MHC restricted cytolytic activity and may be similar to other T3+NK-like cells whose T-cell receptors have not yet been detinitively characterized (39, 72, 73, 74).

As NK-like lymphoyctes, they may participate in host immune surveillance against realignancy. The specificity of lysis observed suggests that the possibility of TCR γ mediated antigen-specific recognition of some but not all tumour targets. As anti-T3 mAb could trigger nonspecific lysis of some target cells or alternatively block specific lysis of other targets, the T3 molecule on these cells appears to be functional.

1. Allison, J. P., McIntyre, B. W. & Block, D. J. Immunol. 128, 2293–2300 (1982).
2. Meuer, S. C., Fitzgerald, K. A., Hussey, R. E., Hodgdon, J. C., Schlossman, S. F. & Reinherz, E. L. J. Exp. Med. 157, 705–719 (1983).
3. Haskins, K., Kubo, R., White, J., Pigeon, M., Kappler, J. & Marrack, P. J. Exp. Med. 157, 1149–1169 (1983).
4. Yanagi, Y., Yoshikai, Y., Leggett, K., Clark, S. P., Aleksander, I. & Mak, T. W. Nature 308, 145–149 (1984).
5. Hedrick, S. M., Nielson, E. A., Kavaler, J., Cohen, D. I. & Davis, M. M. Nature 308, 153–158 (1984).
6. Chien, Y., Becker, D. M., Lindsten, T., Okamura, M., Cohen, D. I. & Davis, M. M. Nature 312, 31–35 (1984).
7. Saito, H., Kranz, D. M., Takagaki, Y., Hayday, A. C., Eisen, H. N. & Tonegawa, S. Nature 312, 36–40 (1984).
8. Sim, G. K., Yague, J., Nelson, J., Marrack., J. Nature 312, 771–775 (1984).
9. Reinherz, E. L., Meuer, S. C., Fitzgerald, K. A., Hussey, R. E., Hodgdon, J. C., Acuto, O. & Schlossman, S. F. Proc. Natl. Acad. Sci U.S.A. 80, 4104–4108 (1983).
10. Oettgen, H. C., Kappler, J., Tax, W. J. M. & Terhorst, C. J. Biol. Chem 259, 12,039–12,048 (1984).
11. Weiss, A. & Stobo, J. D. J. Exp. Med. 160, 1284–1299 (1984).
12. Brenner, M. B., Trowbridge, I. S. & Strominger, J. L. Cell 40, 183–190 (1985).
13. Allison, J. P. & Lanier, L. L. Nature 314, 107–109 (1985).
14. Samelson, L. E. & Schwartz, R. H. Immunol. Rev. 81, 131–144 (1984).
15. Saito, H., Dranz, D. M., Takagaki, Y., Hayday, A. C., Eison, H. N. & Tonegawa, S. Nature 309, 757–762 (1984).
16. Kranz, D. M., Saito, H., Heller, M., Takagaki, Y., Haas, W., Eisen, H. N. & Tonegawa, S. Nature 313, 752–755 (1985).
17. Hayday, A. C., Saito, H., Gillies, D., Kranz, D. M., Tanigawa, G., Eisen, H. N. & Tonegawa, S. Cell 40, 259–269 (1985).
18. Lefranc, M-P & Rabbits, T. H. Nature 316, 464–466 (1985).
19. Murre, C., Waldmann, R. A., Morton, C. C., Bongiovanni, K. F., Waldman, T. A., Shows, T. B. & Seidman, J. G. Nature 316, 549–552 (1985).
20. Quertermous, T., Murre, C., Dialynas, D., Duby, A. D., Strominger, J. L., Waldman, T. A. & Seidman, J. G. Science 231, 252–255 (1986).
21. LeFranc, M-P, Forster, A., Baer, R., Stinson, M. A. & Rabbitts, T. H. Cell 45, 237–246 (1986).
22. Iwamoto, A., Rupp, F., Ohashi, P. S., Walker, C. L., Pircher, H., Joho, R., Hengartner, H. & Mak, T. W. J. Exp. Med. 163, 1203–1212 (1986).
23. Zauderer, M., Iwamoto, A. & Mak, T. W. J. Exp. Med. 163, 1314–1318 (1986).
24. Yague, J., White, J., Coleclough, C., Kappler, J., Palmer, E. & Marrack, P. Cell 42, 81–87 (1985).
25. Dembic, Z., Haas, W., Weiss, S., McCubrey, J., Keller, H., von Boehmer, H. & Steinmetz, M. Nature 320, 232–238 (1986).
26. Hedrick, S. M. et al. Proc. Natl. Acad. Sci. U.S.A. 82, 531–535 (1985).
27. Blanckmeister, C. A., Yamamoto, K., Davis, M. M. & Hammerling, G. J. J. Exp. Med. 162, 851–863 (1985).
28. Brenner, M. B., Trowbridge, McLean, J. & Strominger, J. L. J. Exp. Med. 160, 541–551 (1984).
29. Tax, W. J. M., Willens, H. W., Reekers, P. P. M., Capel, P. J. A. & Koene, R. A. P. Nature 304, 445–447 (1983).
30. Spits, H., Borst, J., Tax, W., Capel. P. J. A., Terhorst, C. & de Vries, J. E. J. Immunol. 135, 1922–1228 (1985).
31. Griscelli, C., Durandy, A., Virelizier, J. L. et al. (1980) In: Seligmann, M. & Hitzig, H. (eds) Primary immunodeficiencies, Elsevier, North-Holland pp 499–504.
32. Hadman, M. R., Dopfer, R. Hans-Harmut, P. & Neithammer, D. (1984) In: Griscelli, C., Vossen, J. (eds) Progress in immunodeficiency research and therapy I. Elsevier Science Publishers B. V., Amsterdam pp 43–50.
33. Levin, L. S., Perrin, J. C. S, Ose, L., Dorst J. P., Miller, J. D. & McKusick, V. A. J. Ped. 90, 55–61 (1977).
34. Brenner, M. B., McLean, J., Yang, S. Y., Poel, J. J., Pious, D. & Strominger, J. L. J. Immunol. 135, 384–390 (1985).
35. Yasunobu, Y., Anatoniou, D., Clark, S. P., Yanagi, Y., Sangster, R., Van den Elsen, P., Terhorst, C. & Mak, T. Nature 312, 521–524 (1984).
36. Dialynas, D. P., Murre, C., Quertermous, T., Boss, J. M., Leiden, J. M., Seidman, J. G. & Strominger, J. L. Proc. Natl. Acad. Sci. U.S.A. 83, 2619–2623 (1986).
37. Raulet, D. H., Garman, R. D., Saito, H. & Tonegawa, S. Nature 314, 103–107 (1985).
38. Snodgrass, H. R., Dembic, Z., Steinmetz, M. & von Boehmer, H. Nature 315, 232–233 (1985).
39. De la Hera, A., Toribio, M. L., Marquez, C. & Martinez-A., C. Proc. Natl. Acad. Sci. U.S.A. 82, 6268–6271 (1985).
40. Beverley, P. C. & Callard, R. E. Eur. J. Immunol. 11, 329–334 (1981).
41. Krangel, M. S. EMBO J. 4, 1205–1210 (1985).
42. Leiden, J. M., Fraser, J. D. & Strominger, J. L. In press, Immunogenetics (1986).
43. Leiden, J. M. & Strominger, J. L. In press, Proc. Natl. Acad. Sci. U.S.A. (1986).
44. Erickson, B. W. & Merrifield, R. B. (1976) In: Neurath, H. & Hill, R. L. (eds) The proteins. Academic Press, N.Y. pp 255–527.
45. Liu, F-T, Zinnecker, M. Hamaoka, T. & Katz, D. H. Biochem. 18, 690–697 (1979).
46. Brenner, M. B., et al. (manuscript in preparation).
47. Kenneth, R. H., McKern, T. J. and Bechtol, K. B. (eds) Monoclonal Antibodies: a new dimension in biological anlaysis. Plenum Press, N.Y. (1980).

48. Ischimori, Y., Kurokawa, T., Honda, S., Suzuki, N., Wakimasu, M. and Tsukamoto, K., J. Immun. Method. 80, 55-66 (1985).
49. Royer, H. D., Bensussan, A., Acuto, O. and Reinherz, E. L., J. Exp. Med. 160: 947-953 (1984).
50. Acuto, O., Fabbi, M., Smart, J., Poole, C. B., Protentis, J., Royer, H. D., Schlossman, S. F. and Reinherz, E. L., Proc. Natl. Acad. Sci. U.S.A., 81, 3851-3855 (1984).
51. Maniatis, T., Fritsch, E. and Sambrook, F., *Molecular Cloning, A Laboratory Manual,* Cold Spring Harbor Laboratory, Cold Spring Harbor, N.Y. 11724 (1982).
52. Schreier, M., Kohler, G., Hengartner, H., Berek, C., Trucco, M. and Formi, L., *Hybridoma Techniques,* Cold Spring Harbor Laboratory, Cold Spring Harbor, N.Y. 11724 (1980).
53. Yelton, D. E., Desaymard, C. and Scharff, M. D., Hybridoma 1, 5-11 (1981).
54. Brenner, M. B., McLean, J. and Strominger, J. L., Feb. Proc. 45, 1292 (1986).
55. Hopp, T. P., and Wood, K. R., Proc. Natl. Acad. Sci. U.S.A. 78, 3824-3828 (1981).
56. Kyte, J. and Doolittle, R. F., J. Mol. Biol. 157, 105-132 (1982).
57. Geysen, H. M., Barteling, S. J. and Meloen, R. H., Proc. Natl. Acad. Sci. U.S.A. 82, 178-182 (1985).
58. Barnstable, C. J. et al., Cell 14, 9-20 (1978).
59. Bushkin, Y., et al., J. Exp. Med. 164, 458-473 (1986).
60. Yang, S. Y., et al., Immunogenetics 19, 217-231 (1984).
61. Spear, B. T., et al., J. Exp. Med. 162, 1802-1810 (1985).
62. Gorga, J. C., et al., Meth. Enzym. 106, 607-613 (1984).
63. Chen, Y. X., et al., Hum. Immun. 10, 221-235 (1984).
64. Samelson, L. E., et al., PNAS U.S.A. 82, 1969-1973 (1985).
65. Krangel, M. S., et al., Cell 18, 979-991 (1979).
66. Bonner, W. J. and Laskey, R. A., Eur. J. Biochem 46, 83-88 (1974).
67. Southern, E. M., J. Molec. Biol. 98, 503-517 (1975).
68. Duby, A. D. and Seidman, J. G. PNAS U.S.A. 83, 4890-4894 (1986).
69. Weiss, A., et al., PNAS U.S.A. 83, 6998-7002 (1986).
70. Bank, I., et al., Nature 322, 179-181 (1986).
71. Quertermous, T., et al., J. Immunol. (in press).
72. Nowill, A., et al., J. Exp. Med. 163, 1601-1606 (1986).
73. Lanier, L. L., et al., J. Exp. Med. 164, 339-344 (1986).
74. Moingeon, P., et al., Nature 323, 638-640 (1986).

What is claimed is:

1. A purified, isolated polypeptide which comprises a δ chain of a T cell antigen receptor, which chain is characterized by
   (a) being associated in a complex with the T3 antigen when found on the surface of a T cell,
   (b) not being reactive with antibodies to the alpha, beta T cell antigen receptor,
   (c) not being reactive with monoclonal antibody βF1, and
   (d) not being reactive with antibodies to the γ chain of the T cell antigen receptor.
2. A polypeptide of claim 1 which has at least one intrachain, covalent, disulphide linkage.
3. A polypeptide of claim 1 having a molecular weight of about 40,000 daltons.
4. A polypeptide of claim 1, which is a δ chain of a human T cell antigen receptor.
5. An antibody reactive with at least one δ chain of a T cell antigen receptor of claim 1.
6. An antibody of claim 5 reactive with one δ chain of a T cell antigen receptor.
7. An antibody of claim 5 reactive with more than one δ chain of a T cell antigen receptor.
8. A polyclonal antibody of claim 5.
9. A monoclonal antibody of claim 5.
10. A purified, isolated polypeptide which comprises a γ chain of a T cell antigen receptor, which chain is characterized by
    (a) being associated in a complex with the T3 antigen when found on the surface of a T cell,
    (b) not being reactive with antibodies to the alpha, beta T cell antigen receptor,
    (c) not being reactive with monoclonal antibody βF1, and
    (d) being reactive with an antibody to the γ chain of the T cell antigen receptor.
11. A polypeptide of claim 11 wherein the γ chain has a molecular weight of about 55,000 daltons as determined by denaturing polyacrylamide gel electrophoresis.
12. A polypeptide of claim 10, which is a γ chain of a human T cell antigen receptor.
13. A purified, isolated complex which comprises two γ chains of the T cell antigen receptor of claim 32 associated with each other.
14. A complex of claim 13 wherein the two γ chains of a T cell antigen receptor are associated with each other through at least one interchain, covalent, disulphide linkage.
15. A complex of claim 13 wherein the two γ chains of a T cell antigen receptor are noncovalently associated with each other.
16. A complex of claim 13 wherein the two γ chains of a T cell antigen receptor have the same constant domain.
17. A complex of claim 13 wherein the two γ chains of a T cell antigen receptor have different constant domains.
18. An antibody reactive with at least one γ chain of a T cell antigen receptor of claim 10.
19. An antibody of claim 18 reactive with one γ chain of a T cell antigen receptor.
20. An antibody of claim 18 reactive with more than one γ chain of a T cell antigen receptor.
21. A polyclonal antibody of claim 18.
22. A monoclonal antibody of claim 18.
23. A purified, isolated complex which comprises a δ chain polypeptide of a T cell antigen receptor, which chain is characterized by
    (a) being associated in a complex with the T3 antigen when found on the surface of a T cell,
    (b) not being reactive with antibodies to the alpha, beta T cell antigen receptor,
    (c) not being reactive with monoclonal antibody βF1, and
    (d) not being reactive with antibodies to the γ chain of the T cell antigen receptor;
and a γ chain polypeptide of a T cell antigen receptor, which γ chain is characterized by
    (a) being associated in a complex with the T3 antigen when found on the surface of a T cell, (b) not being reactive with antibodies to the alpha, beta chain of the T cell antigen receptor, (c) not being reactive with monoclonal antibody βF1, and (d) being reactive with antibodies to the γ chain of the T cell antigen receptor.

24. A complex of claim 23 wherein the δ chain of a T cell antigen receptor has a molecular weight of about 40,000 daltons as determined by denaturing polyacrylamide gel electrophoresis and the γ chain of a T cell antigen receptor has a molecular weight of about 55,000 daltons as determined by denaturing polyacrylamide gel electrophoresis.

25. A complex of claim 23, wherein the δ chain of a T cell antigen receptor is a δ chain of a human T cell antigen receptor and the γ chain of a T cell antigen receptor is a γ chain of a human T cell antigen receptor.

26. A complex of claim 23, wherein the δ chain polypeptide and the γ chain polypeptide are associated with each other through at least one interchain, covalent, disulphide linkage.

27. A complex of claim 23, wherein the δ chain polypeptide and the γ chain polypeptide are noncovalently associated with each other.

28. An antibody reactive with at least one γ, δ T cell antigen receptor complex of claim 23.

29. An antibody of claim 23 reactive with one γ, δ T cell antigen receptor complex.

30. An antibody of claim 28 reactive with more than one γ, δ T cell antigen receptor complex.

31. A polyclonal antibody of claim 28.

32. A monoclonal antibody of claim 30.

33. A polypeptide of claim 10 wherein the γ chain of a T cell antigen receptor has a molecular weight of about 40,000 daltons as determined by denaturing polyacrylamide gel electrophoresis.

34. A polypeptide of claim 10 wherein the γ chain of the T cell antigen receptor comprises a nonglycosylated polypeptide backbone having a molecular weight of about 31,000 daltons as determined by denaturing polyacrylamide gel electrophoresis.

35. A polypeptide of claim 10 wherein the γ chain of the T cell antigen receptor comprises a nonglycosylated polypeptide backbone having a molecular weight of about 40,000 daltons as determined by denaturing polyacrylamide gel electrophoresis.

36. A complex of claim 23 wherein the δ chain of a T cell antigen receptor has a molecular weight of about 40,000 daltons as determined by denaturing polyacrylamide gel electrophoresis and the γ chain of a T cell antigen receptor has a molecular weight of about 40,000 daltons as determined by denaturing polyacrylamide gel electrophoresis.

37. The polypeptide of claim 10 which is glycosylated.

38. The polypeptide of claim 11 which is glycosylated.

39. The complex of claim 24 in which the γ chain is glycosylated.

40. The polypeptide of claim 33 in which the γ chain is glycosylated.

* * * * *